US007829708B2

(12) United States Patent
Roberts et al.

(10) Patent No.: US 7,829,708 B2
(45) Date of Patent: Nov. 9, 2010

(54) METABOLICALLY INERT ANTIFOLATES FOR TREATING DISORDERS OF ABNORMAL CELLULAR PROLIFERATION AND INFLAMMATION

(75) Inventors: Michael J. Roberts, Williamsburg, VA (US); Simon Pedder, Charlotte, NC (US)

(73) Assignee: Chelsea Therapeutics, Inc., Charlotte, NC (US)

( * ) Notice: Subject to any disclaimer, the term of this patent is extended or adjusted under 35 U.S.C. 154(b) by 1273 days.

(21) Appl. No.: 11/223,433

(22) Filed: Sep. 8, 2005

(65) Prior Publication Data

US 2006/0111272 A1    May 25, 2006

Related U.S. Application Data

(60) Provisional application No. 60/607,883, filed on Sep. 8, 2004, provisional application No. 60/611,482, filed on Sep. 20, 2004.

(51) Int. Cl.
*C07D 239/72* (2006.01)
*A61K 31/519* (2006.01)

(52) U.S. Cl. .................................. 544/283; 514/258.1
(58) Field of Classification Search .............. 514/258.1; 544/283
See application file for complete search history.

(56) References Cited

U.S. PATENT DOCUMENTS

| 4,996,207 | A | | 2/1991 | Nair et al. |
| 5,028,608 | A | | 7/1991 | Taylor et al. |
| 5,073,554 | A | | 12/1991 | Nair |
| 5,248,775 | A | | 9/1993 | Taylor et al. |
| 5,344,932 | A | | 9/1994 | Taylor |
| 5,534,518 | A | | 7/1996 | Henrie, II et al. |
| 5,550,128 | A | | 8/1996 | Nair et al. |
| 5,593,999 | A | | 1/1997 | Nair et al. |
| 5,866,580 | A | | 2/1999 | Gangjee |
| 5,912,251 | A | | 6/1999 | Nair |
| 6,048,736 | A | * | 4/2000 | Kosak ......................... 436/536 |
| 6,667,318 | B2 | | 12/2003 | Burdick et al. |
| 7,060,825 | B2 | | 6/2006 | Wu et al. |
| 7,612,071 | B2 | * | 11/2009 | Kamen et al. ................ 514/249 |
| 2001/0034333 | A1 | * | 10/2001 | Kosak .......................... 514/44 |
| 2002/0077280 | A1 | * | 6/2002 | Judice et al. .................... 514/8 |
| 2003/0162721 | A1 | * | 8/2003 | Mehlem ....................... 514/18 |
| 2003/0181635 | A1 | | 9/2003 | Kochat et al. |
| 2004/0092739 | A1 | | 5/2004 | Xiao et al. |
| 2005/0020833 | A1 | | 1/2005 | Wu et al. |
| 2006/0111272 | A1 | | 5/2006 | Roberts et al. |
| 2006/0160751 | A1 | | 7/2006 | McGuire |

FOREIGN PATENT DOCUMENTS

| EP | 0 239 362 | 9/1987 |
| EP | 0 340 905 | 11/1989 |
| WO | WO 93/13079 | 7/1993 |
| WO | WO-02/081455 A1 | 10/2002 |

OTHER PUBLICATIONS

Merriam-Webster's Collegiate Dictionary, Merriam-Webster Incorporated: Springfield, Massachusetts, 1993, pp. 311 and 996.*
Baugh et al., "Polygammaglutamyl Metabolites of Methotrexate," *Biochemical and Biophysical Research Communications*, 1973, pp. 27-34, vol. 52, No. 1.
Jackman, "Antifolate Drugs In Cancer Therapy," *Book Review: Reprints from Current Trends, Drug Discovery Today*, 1999.
Montgomery et al., "Design and Synthesis of Folate Analogs as Antimetabolites In Folate Antagonists as Therapeutic Agents," *Biochemistry, Molecular Actions and Synthetic Designs*, 1984, pp. 219-261, vol. 1.
Moran et al. "Relative Substrate Activities of Structurally Related Pteridine, Quinazoline, and Pyrimidine Analogs for Mouse Liver Folylpolyglutamate Synthetase," *Molecular Pharmacology*, 1989, pp. 736-743, vol. 36, No. 5.
Nair et al., "Metablism Blocked Classical Folate Analog Inhibitors of Dihydrofolate Reductase-1: Synthesis and Biological Evaluation of Mobiletrex," *Medicinal Chemistry Research*, 1999, pp. 176-185, vol. 9, No. 3.
Yan et al., "Folic Acid Analogs . III. N-(2[2-(,4-diamino-6-quinazolinyl)ethyl] benzoyl)-L-glutamic acid," *J. Heterocyclic Chem.*, 1979, 541-544, vol. 16.
Abraham et al., "Aldehyde Oxidase Mediated 7-Hydroxylation of Antifolates and Its Therapeutic Relevance," *Cellular Pharmacology*, 1996, vol. 3, pp. 29-34.
Abraham et al., "Folate Analogues. 34. Synthesis and Antitumor Activity of Non-Polyglutamylatable Inhibitors of Dihydrofolate Reductase," *J. Med. Chem.*, 1991, vol. 34, pp. 222-227.
Amato et al., "Metabolism-Based Antifolate Drug Design: MDAM and MTREX," *Pharmacology and Therapeutics in the New Millennium*, 2001, pp. 204-212, Narosa Publishing House, New Delhi, India.
Broxterman et al., "Cancer Research 2001: Drug Resistance, New Targets and Drug Combinations," *Drug Resistance Updates*, 2001, vol. 4, pp. 197-209.
Bryant et al., "Metabolism-Blocked Antifolate-2," *Proc. Am. Assoc. Cancer Res.*, 1999, vol. 40, p. 293 (Abstract No. 1944).
Degraw et al., "Synthesis and Antifolate Activity of 8,10-Dideazaminopterin," *J. Het. Chem.*, 1982, vol. 19, pp. 1587-1588.
Gangjee et al., "Nonclassical 2,4-Diamino-8-Deazafolate Analogues as Inhibitors of Dihydrofolate Reductases from Rat Liver, *Pneumocystis carinii*, and *Toxoplasma gondii*," *J. Med. Chem.*, 1996, vol. 39(9), pp. 1836-1845.

(Continued)

*Primary Examiner*—Johann R Richter
*Assistant Examiner*—James H Alstrum Acevedo
(74) *Attorney, Agent, or Firm*—Womble Carlyle Sandridge & Rice, PLLC

(57) ABSTRACT

The present invention provides compositions and methods for the treatment of disorders of abnormal cell proliferation and/or inflammation, such as psoriasis and inflammatory bowel disease, in a human or other host animals.

15 Claims, 2 Drawing Sheets

OTHER PUBLICATIONS

Kisliuk, "Deaza Analogs of Folic Acid as Antitumor Agents," *Current Pharmaceutical Design*, 2003, vol. 9(31), pp. 2615-2625.

Lemanske, "Inflammation in Childhood Asthma and Other Wheezing Disorders," *Pediatrics*, 2002, vol. 109(2), pp. 368-372.

McGuire, "Anticancer Antifolates: Current Status and Future Directions," *Current Pharmaceutical Design*, 2003, vol. 9(31), pp. 2593-2613.

Nagayama et al., "Eosinophils and Basophilic Cells in Sputum and Nasal Smears Taken from Infants and Young Children during Acute Asthma," *Pediatr. Allergy Immunol.*, 1995, vol. 6, pp. 204-208.

Nair et al., "Metabolism-Blocked Antifolates-1," *Proc. Am. Assoc. Cancer Res.*, 1998, vol. 39, p. 431 (Abstract No. 2938).

Nair et al., "Polyglutamylation as a Determinant of Cytotoxicity of Classical Folate Analogue Inhibitors of Thymidylate Synthase and Glycinamide Ribonucleotide Formyltransferase," *Cellular Pharmacology*, 1994, vol. 1, pp. 245-249.

Renouard et al., "Functionalized Tetradentate Ligands for Ru-Sensitized Solar Cells," *Tetrahedron*, 2001, vol. 57, pp. 8145-8150.

Rosowsky et al., "Analogues of Methotrexate and Aminopterin with γ-Methylene and γ-Cyano Substitution of the Glutamate Side Chain: Synthesis and in Vitro Biological Activity," *J. Med. Chem.*, 1991, vol. 34, pp. 203-208.

Shilai et al., "Selective Metallation of Thiophene and Thiazole Rings with Magnesium Amide Base," *J. Chem. Soc.*, Perkin Trans. 1, 2001, pp. 442-444.

Takimoto, "New Antifolates: Pharmacology and Clinical Applications," *The Oncologist*, 1996, vol. 1, pp. 68-81.

Grant Proposal, "Mobiletrex (M-Trex) for the Prevention and/or Treatment of Coronary Heart Disease", American Heart Association, Jan. 23, 2003, 35 pages.

Grant Application, "Anti-inflammatory Antifolate Therapy for Heart Disease", Department of Health and Human Services, Jan. 23, 2003, 27 pages.

Choi et al., "Methotrexate and Mortality in Patients with Rheumatoid Arthritis: A Prospective Study", *The Lancet*, 2002, pp. 1173-1177, vol. 359, Abstract only.

Dessein et al., "Effects of Disease Modifying Agents and Dietary Intervention on Insulin Resistance and Dyslipidemia in Inflammatory Arthritis: A Pilot Study", *Arthritis Res.* 2002, pp. 1-7, vol. 4, No. 6.

Park et al., "Effects of Antirheumatic Therapy on Serum Lipid Levels in Patients with Rheumatoid Arthritis: A Prospective Study", *Am. J. Med.*, 2002, pp. 188-193, vol. 113, No. 3, Abstract only.

McGuire, et al., "Metabolism-blocked Antifolates as Potential Antirheumatoid Arthritis Agents: 4-Amino-4-deoxy-5,8,10-trideazapteroyl—D,L-4'-methyleneglutamic Acid (CH-1504) and Its Analogs," *Biochemical Pharmacology*, 2009, pp. 1161-1172, vol. 77, No. 7.

Nair et al., "Metabolism-Blocked Antifolates, 3: Enantiomers of 4'methylene-5,8,10-Trideazaaminopterin (M-Trex)," *Proceedings of the American Association for Cancer Research Annual Meeting*, 2001, pp. 294, vol. 42. (Abstract No. 1583).

\* cited by examiner

Figure 1: Illustration of the Metabolically Inert Antifolate

METABOLICALLY INERT ANTIFOLATES FOR TREATING DISORDERS OF ABNORMAL CELLULAR PROLIFERATION AND INFLAMMATION

This application claims priority to U.S. Provisional application Nos. 60/607,883, which was filed on Sep. 8, 2004, and 60/611,482, which was filed on Sep. 20, 2004, which is hereby incorporated by reference in their entirety.

FIELD OF THE INVENTION

The invention is in the area of pharmaceutical chemistry, and is in particular, metabolically inert etiolate compounds for the prevention and treatment of disorders of abnormal cell proliferation and/or inflammation, such as psoriasis and Crohn's disease.

BACKGROUND OF THE INVENTION

Disorders of abnormal cell proliferation are characterized by inappropriate growth or multiplication of one or more cell types. They include malignant (i.e., cancer) as well as non-malignant disorders. Many of these diseases also include an inflammatory component. Psoriasis represents one type of non-malignant disorder of abnormal cell proliferation. The disorder is characterized by psoriatic skin plaques representing highly localized sites of deregulated growth and inflammation. While the cause of psoriasis is poorly understood, it is thought to involve both a genetic and environmental component. Moderate-to-severe psoriasis has traditionally been treated with systemic therapies such as cyclosporine, methotrexate, retinoids, and phototherapy (i.e., ultraviolet B, psoralen plus ultraviolet A). Traditional treatments, however, suffer limitations including significant side effects, lack of durable efficacy, and inconvenient administration schedules.

Uncontrolled or inappropriate chronic inflammatory responses are characteristic of a variety of diseases and disorders. Inflammatory bowel disease (IBD), including both Crohn's disease and ulcerative colitis, provides one example of an inflammatory disorder. IBD affects the quality of life of more than one million Americans. At present, aminosalicylates (5-ASA), corticosteroids, immune modifiers and antibiotics are used to treat Crohn's disease. Current therapies, however, are ineffective in many patients and present significant side effects including slow onset of action and toxicity.

Antifolates are compounds that interfere with various stages of foliate metabolism. An intact foliate enzyme pathway is important to maintain de novo synthesis of the building blocks of DNA, as well as of the important amino acids. Antifolate targets include the various enzymes involved in foliate metabolism, including (i) dihydrofolate reductase (DHFR); (ii) thymidylate synthase (TS); (iii) folylpolyglutamyl synthase; and (iv) glycinamide ribonucleotide (GAR) and aminoimidazole carboxamide ribonucleotide (AICAR) transformylases.

Antifolates are folate acid analogs. For a general review of antifolates, see Montgomery JA and Piper Jr. Design and Synthesis of Folate Analogs as Antimetabolites. In Folate Antagonists as Therapeutic Agents. Volume 1: Biochemistry, Molecular Actions and Synthetic Design. Eds. Sirotnak F M, Burchall J J, Ensminger W D and Montgomery J A. Academic Press. pp 219-261, 1984; Thomas W. *Current Oncology Reports* (2003) 5:114-125; Graffner NM. Approaches to Soft Drug Analogues of Dihydrofolate Reductase Inhibitors, in Comprehensive Summaries of Uppsala Dissertations from the Faculty of Pharmacy 252 (2001); Beale, P., and Clarke, S. Tomudex. Clinical development. In: A. L. Jackman (ed.), Antifolate Drugs in Cancer Therapy, pp. 167-191. Allegra C J: Antifolates, in Chabner B A, Collins J M (eds): Cancer Chemotherapy: Principles & Practice, pp 110-153. Philadelphia, Lippincott, 1990.

Folic acid contains a pteridine ring, para-aminobenzoic acid and a glutamate residue.

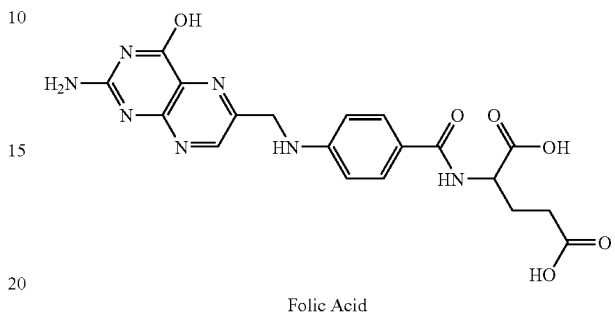

Folic Acid

Methotrexate, a DHFR inhibitor, is among the earliest antifolates. It is a classical antifolate, meaning it is characterized by a p-aminobenzogylglutamic acid side chain, and closely resembles the folic acid molecule. MTX differs from folic acid by the substitution of an amino group for a hydroxyl at the 4-position of the pterdine ring and by the methylation of the amine of the para-aminobenzoic moeity. The substitution of an amino group for a hydroxyl at the 4-position of the pterdine ring changes the enzyme substrate into a tight binding inhibitor of DHFR.

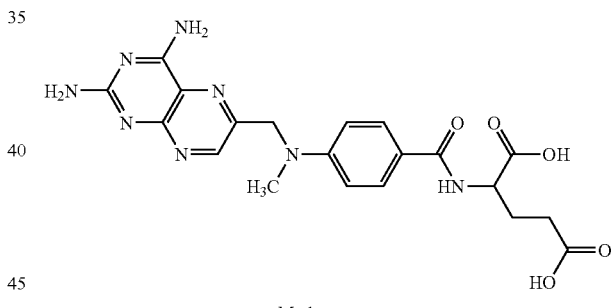

Methotrexate

Both MTX and naturally occurring folate compounds undergo intracellular metabolism to polyglutamate derivatives. This polyglutamylation is catalyzed by the enzyme folylpolyglutamyl synthase (FPGS), which attaches up to six glutamate residues to the molecule, which helps to trap it within the cell. Polyglutamylation of MTX occurs more slowly compared to naturally occurring antifolates, but the resulting methotrexate polyglutamylates have extremely long intracellular half-lives, and can be detected in some tissues more than several months after a single drug administration (Takimoto C H et al. *Oncology* (1995) 9(7): 649-656).

The most common use of MTX is as an anti-cancer drug. MTX is curative of choriocarcinoma and Burkett's lymphoma. It has also widely used as a single agent or in combination with other drugs for the treatment of various forms of human cancer. More recently, MTX has been shown to have anti-inflammatory and immunosuppressive properties with accompanying activity against autoimmune disorders. MTX is now widely prescribed as an immunosuppressive agent in the treatment of autoimmune diseases, including rheumatoid arthritis (Weinblatt M E et al. *N. Ensl. J. Med.* (1985) 312: 818; Wilke W S (Ed). Methotrexate Therapy in Rheumatic Disease. Marcel Dekker, Inc. (1989). Intrinsic and acquired resistance to MTX and other antifolate analogues limits their clinical effectiveness, however. Apart from resistance, major limitations of MTX treatment include bone marrow toxicity, gastrointestinal ulceration and liver and kidney damage.

A number of antifolates have been designed to overcome these limitations. Rational design has focused, for example, on the development of antifolates with greater lipid solubility and/or improved transport characteristics relative to methotrexate (Takimoto C H et al. Oncology (1995) 9(7); 649-656). Representative non-classical agents include trimetrexate and piritrexim (Kamen B A et al. *J. Biochem. Pharmacol.* (1984) 33: 1697-1984; Duch D S et al. *Cancer Res.* (1982) 42: 3987-3994). Unlike classical antifolates, non-classical antifolates lack the glutamate moiety, and therefore do not require carrier-mediated cellular uptake. These lipophilic antifolates are used against opportunistic infections (e.g., *Pneumocystic carinii* pneumonia, PCP) in individuals with AIDS and other disorders of the immune system and have undergone extensive clinical testing as anticancer agents.

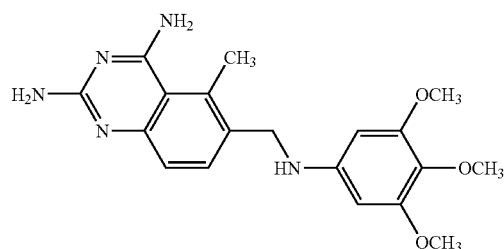

Trimetrexate

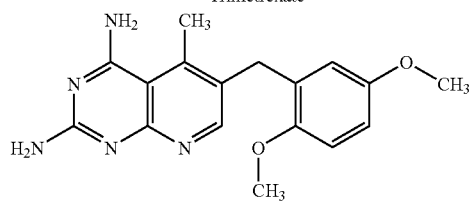

Piritrexim

Other antifolates in clinical development specifically target folate-dependent enzymes such as TS or GARFT, thereby directly affecting pools of nucleotides available for DNA synthesis (Takemura Y. et al. *Anti-Cancer Drugs* (1997) 8: 3-16; Habeck L L et al. *Cancer Res* (1994) 54: 1021-1026). Direct and specific TS inhibitors have been studied as potential anticancer drugs (Stout T J et al. *Biochemistry* (1999) 38: 1607-1617). Of these, Tomudex (raltitrexed; ZD1649), [N-{5-[N-(3-,4-dihydro-2-methyl-4-oxoquinazoline-6-ylmethyl)-N-methylamine]-2-theroyl}-L-glutei acid], is one of the most extensively evaluated and has been approved for treatment in Europe (Van Custom *Euro. J. Cancer*, (1999) 35(Suppl.1): 1-2; Jack man AL. Invest. New Drugs, (1996) 14: 305-316). Comdex undergoes substantial polyglutamylation within the cell. Comdex and its polyglutamates do not appear to inhibit DHFR, GAR or AICAR transformylase, suggesting that the drug is a pure TS inhibitor.

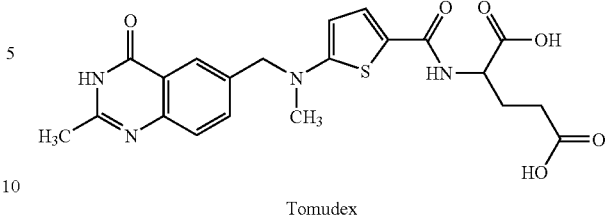

Tomudex

Inhibitors of glycinamide ribotide formyltransferase (GARFT) have also been developed. Lometrexol ((5,10-dideazatetrahydrofolate [DDATHF]) is a specific GARFT inhibitor that has shown anti-tumor properties (Habeck L L et al. *Cancer Res*. (1994) 54: 1021-1026). Early clinical trials, however, were confounded by cumulative myelosuppression that prevented repetitive administration (Roberts J D. *Cancer Chemother Pharmacol.* (2000) 45(2):103-10). LY309887 (6R-2',5'-thienyl-5,10-dideazatetrahydrofolic acid) is a thiophene analogue of lometrexol, is a second generation GARFT inhibitor (Mendelsohn L G. *Investig. New Drugs* (1996) 14: 287-294).

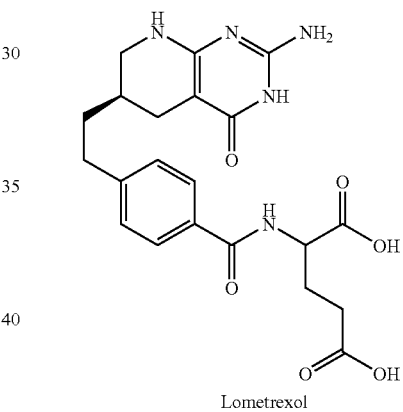

Lometrexol

In 1991, Nair et al. demonstrated that contrary to the widely accepted notion, polyglutamylation of classical antifolates is not essential for anti-tumor activity and further, that this metabolic transformation is actually undesirable because it may cause the loss of pharmacological control and target specificity of the drug (Nair M G et al. *J. Med. Chem* (1991) 34: 222-227). This new finding let to the discovery of a number of nonpolyglutamylatable classical antifolates (Nair M G et al. *Proc. Amer. Assoc. Cancer. Research.* (1998) 39:431).

U.S. Pat. No. 5,073,554 (Nair) describes methylene-1-deazaaminopterine (MDAM), a nonpolyglutamylatable antifolate compound. MDAM has been developed as an experimental anticancer drug for the treatment of human solid tumors (Cao S. et al. *Clinical Cancer Research* (1996) 2(4): 707-712); Johansen M et al. *Cancer Chemother Pharmacol.* (2004) 53(5):370-6). U.S. Pat. No. 5,550,128 (Nair et al) describes the active enantiomer of MDAM as the one possessing the L-configuration.

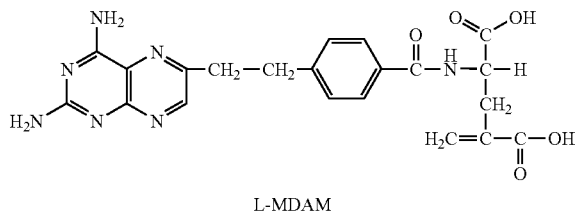

L-MDAM

Further investigation by Nair et al. of the metabolic disposition of certain non-polyglutamylatable antifolates led to the unexpected finding that the presence of the 4-methyleneglutamate moiety modulates the binding of such compounds to the liver enzyme aldehyde oxidase, which mediates their oxidative deactivation to the corresponding 7-hydroxy derivatives (*Cellular. Pharmacology* (1996) 3: 29). U.S. Pat. No. 5,912,251 (Nair) describes metabolically inert classical antifolates, including 4-Amino4-deoxy-5,8,10-trideazapteroyl-4'-methylene glutamic acid, which are non-polyglutamylatable and non-hydroxylatable. They are said to be useful in the treatment of neoplastic disease (leukemia, ascetic and solid tumors), asthma and related anti-inflammatory disease, and for the treatment of rheumatoid arthritis and other autoimmune diseases.

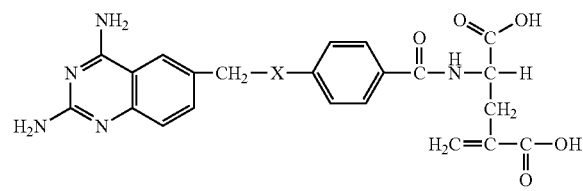

wherein X is $CH_2$, $CHCH_3$, $CH(CH_2CH_3)$, NH, or $NCH_3$.

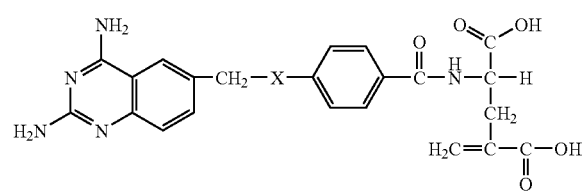

wherein X is $CH_2$.

MTREX

U.S. Pat. No. 5,912,251 to Nair discloses certain antifolate compounds for the treatment of neoplastic diseases, asthma, and/or rheumatoid arthritis.

There remains a strong need to provide effective agents to treat diseases and disorders of abnormal cell proliferation and/or inflammation.

It is therefore an object of the present invention to provide compositions and methods for the treatment of diseases and disorders characterized by abnormal cell proliferation, such as psoriasis.

It is a further object of the present invention to provide compositions and methods for the treatment of diseases and disorders characterized by inflammation, including inflammatory bowel disease.

SUMMARY OF THE INVENTION

The present invention provides metabolically inert antifolate compounds, or pharmaceutically acceptable formulations containing these compounds, for use in the prevention and treatment of disorders characterized by abnormal cell proliferation and/or inflammation, such as psoriasis and Crohn's disease.

A method for the treatment of disorders characterized by abnormal cell proliferation and/or inflammation is also disclosed that includes administering an effective amount of the metabolically inert antifolate compound of the present invention, administered alone or in combination with another anti-proliferation or anti-inflammation agent, optionally in a pharmaceutically acceptable carrier.

In one embodiment, the compound of Formula (I) is provided as well as a method for the treatment of a host with a disease or disorder characterized by non-neoplastic abnormal cell proliferation, non-asthmatic inflammation including, but not limited to, inflammatory bowel disease (e.g., Crohn's disease) and/or chronic obstructive pulmonary disease (COPD), and/or non-rheumatoid arthritic auto-immune disease including, but not limited to, psoriasis, osteoarthritis, and/or multiple sclerosis (MS), comprising administering an effective treatment amount of compound of Formula (I):

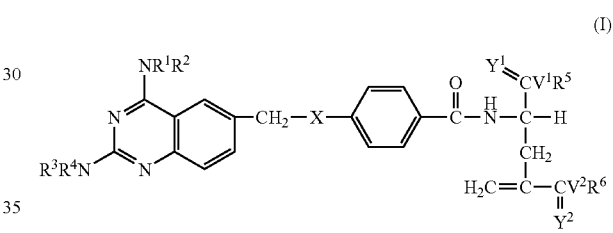

(I)

or its pharmaceutically acceptable salt, ester, salt of an ester, amide, salt or an amide, prodrug, salt of a prodrug, or a steroisomeric, tautomeric or polymorphic form thereof;

wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —C(=Y)V$^-$ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino.

In one embodiment of the present invention, a method for the treatment of a host with a disease or disorder characterized by non-neoplastic abnormal cell proliferation is provided. Diseases or disorders characterized by non-neoplastic abnormal cell proliferation include, but are not limited to, (i) skin disorders including, without limitation, psoriasis (all types), eczema, acne, acne vulgaris, acne inverse, rosacea, common warts, anogenital (venereal) warts, lupus associated skin lesions, dermatitides (e.g., such as atopic dermatitis, contact dermatitis, seborrheic dermatitis and solar dermatitis), keratoses (e.g., seborrheic keratosis, keratosis follicularis, senile keratosis, actinic keratosis, photo-induced keratosis), skin ageing (e.g., photo-induced skin aging), keloids, eukoplakia, lichen planus, keratitis, urticaria, pruritus, hidradenitis, pemphigus vulgaris; (ii) bowel disorders; (iii) blood vessel disorders including, without limitation, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, comeal graft rejection, neuroscular glaucoma land Oster Webber syndrome; (iv) cardiovascular disorders including, for example, hypertension, vasculo-occlusive diseases (e.g., atherosclerosis, thrombosis and restenosis after angioplasty), acute coronary syndromes (e.g., unstable angina, myocardial infarction, ischemic and non-ischemic cardiomyopathies, post-MI cardiomyopathy and myocardial fibrosis, and substance-induced cardiomyopathy), ischemic heart disease; (v) fibrotic disorders including, without limitation, fibrosis and other medical complications of fibrosis which result in whole or in part from the proliferation of fibroblasts, and hepatic cirrhosis; (vi) mesangial disorders including, without limitation, human renal diseases such as glomerulonephritis, diabetic nephropathy, malignant nephrosclerosis, thrombotic microangiopathy syndromes, transplant rejection, and glomerulopathies; (vii) graft-versus-host rejection; (viii) urogenital disorders including, without limitation, endometriosis, benign prostatic hyperplasia, eiomyoma, polycystic kidney disease, and diabetic nephropathy; (ix) disorders of the tissue and joints including, without limitation Raynaud's phenomenon/disease, Sjogren's Syndrome systemic sclerosis, systemic lupus erythematosus, vasculitides, ankylosing spondylitis, osteoarthritis, reactive arthritis, psoriatic arthritis, fibromyalgia; (x) degenerative neurological disorders such as Parkinson's disease and Alzheimer's disease; (xi) virus-induced hyperproliferative diseases including, for example, human papilloma virus-induced disease (e.g., lesions caused by human papilloma virus infection), Epstein-Barr virus-induced disease, acquired immune deficiency syndrome (AIDS)-induced disease, scar formation, genital warts, cutaneous warts, and the like; (xii) pulmonary disorders including, without limitation, chronic obstructive pulmonary disease (COPD), reactive airway disease, pulmonary fibrosis, acute respiratory distress syndrome (ARDS) pulmonary hypertension; (xiii) other diseases and disorders including Behcet's syndrome, Fibrocystic breast disease, fibroadenoma, chronic fatigue syndrome, post-dialysis syndrome, vasculitis, lipid histiocytosis, septic shock, and familial intestinal polyposes such as Gardner syndrome. The compound of Formula (I) can be administered either alone or in combination with one or more other anti-proliferative agent, optionally in a pharmaceutically acceptable carrier to treat a disease or disorder characterized by non-neoplastic abnormal cell proliferation.

In another embodiment of the present invention, a method for the treatment of a host with a disease or disorder characterized by non-asthmatic inflammation is provided. Disorders characterized by non-asthmatic inflammatory diseases associated with abnormal cell proliferation include, but are not limited to, inflammatory bowel disease (IBD) (e.g., Crohn's disease (CD) and ulcerative colitis (UC)), chronic obstructive pulmonary disease (COD), sarcidosis, non-rheumatoid arthritis (e.g., fibromyalgia, fibrositis, myofascil pain, humeral epicondyltitis, frozen shoulder, Tietze's syndrome, fascitis, tendonitis, tenosynovitis, bursitis, juvenile chronic arthristis, spondyloarthropaties, hyperuricemia, and arthristis associated with acute gout, chronic gout and systemic lupus erthematosus, osteoarthristis), multiple sclerosis (MS), proliferative glomerulonephritis, lupus erythematosus, scleroderma, temporal arteritis, thromboangiitis obliterans, mucocutaneous lymph node syndrome, host versus graft, thyroiditis, Grave's disease, antigen-induced airway hyperactivity, pulmonary eosinophilia, Guillain-Barre syndrome, allergic rhinitis, myasthenia gravis, human T-lymphotrophic virus type 1-associated myelopathy, herpes simplex encephalitis, inflammatory myopathies, Goodpasture's syndrome, poststreptococcal and autoimmune renal failure, septic shock, systemic inflammatory response syndrome (SIRS), adult respiratory distress syndrome (ARDS), envenomation, Hashimoto's thyroiditis, autoimmune hemolytic anemias, insulin dependent diabetes mellitus, rheumatic fever, pelvic inflammatory disease (PID), conjunctivitis, dermatitis, bronchitis, rhinitis, and cardiovascular diseases, including restenosis, atherosclerosis, atherosclerotic complications resulting from plaque rupture, severe tissue ischemia, and heart failure. The compound of Formula (I) can be administered either alone or in combination with one or more other antiproliferative agent, optionally in a pharmaceutically acceptable carrier to treat a non-asthmatic inflammation disorder.

In one embodiment, a method for the treatment of psoriasis in a host, including a human, is disclosed that involves administering an effective amount of the compound of Formula (I), administered either alone or in combination with one or more other anti-psoriasis agents, optionally in a pharmaceutically acceptable carrier.

In another embodiment, a method for the treatment of inflammatory bowel disease in a host, including a human, is disclosed that involves administering an effective amount of the compound of Formula (I), administered either alone or in combination with one or more other anti-inflammatory bowel disease agents, optionally in a pharmaceutically acceptable carrier. In one embodiment, the inflammatory bowel disease is Crohn's disease. In another embodiment, the inflammatory bowel disease is ulcerative colitis.

In another embodiment, a method for the treatment of osteoarthritis in a host, including a human, is disclosed that involves administering an effective amount of the compound of Formula (I), administered either alone or in combination with one or more other anti-osteoarthritis agents, optionally in a pharmaceutically acceptable carrier.

In yet another embodiment, a method for the treatment of chronic obstructive pulmonary disease (COPD) in a host, including a human, is disclosed that involves administering an effective amount of the compound of Formula (I), administered either alone or in combination with one or more other anti-COPD agents, optionally in a pharmaceutically acceptable carrier.

In another preferred embodiment, a method for the treatment of multiple sclerosis (MS) in a host, including a human, is disclosed that involves administering an effective amount of the compound of Formula (I), administered either alone or in combination with one or more other anti-MS agent, optionally in a pharmaceutically acceptable carrier.

In an alternative embodiment, the compound of Formula (II) is provided as well as a method for the treatment of a host with a disorder characterized by abnormal cell proliferation, inflammation, and/or auto-immune disease, comprising administering an effective treatment amount of a compound of Formula (II):

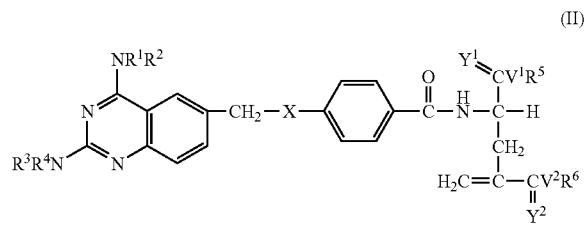

or its pharmaceutically acceptable salt, ester, salt of an ester, amide, salt or an amide, prodrug, salt of a prodrug, or a steroisomeric, tautomeric or polymorphic form thereof;

wherein
X is $CH_2$, $CHCH_3$, $CH(CH_2CH_3)$, NH, $NCH_3$, or $NR^7$
$R^1$, $R^2$, $R^3$, $R^4$, and $R^7$ are independently selected from H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;
$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —C(=Y)V⁻ or —C(=Y)VH moiety when administered in vivo;
each $Y^1$, $Y^2$, and $Y^3$ independently is O, S or $NJ^1$;
each $V^1$ and $V^2$ independently is O, S or $NJ^1$
each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;
each $J^1$, $J^2$ and $J^3$ independently are hydrogen, alkyl, alkenyl, alkynyl, alkaryl, cycloalkyl, aryl, cycloaryl, heterbalkyl, heterocycle, heteroaryl, hydroxyl, alkoxy, or amine; and
each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino;
such that, if $Y^1$ and $Y^1$ are both oxygen, and $V^1$ and $V^2$ are both oxygen, then at least one of $R^1$, $R^2$, $R^3$, $R^4$, $R^5$, $R^6$, and $R^7$ is not H.

In one embodiment, a method for the treatment of abnormal cell proliferation in a host, including a human, is disclosed that involves administering an effective amount of the compound of Formula (II), administered either alone or in combination with one or more other anti-abnormal cell proliferation agents, optionally in a pharmaceutically acceptable carrier.

In one embodiment, a method for the treatment of an autoimmune disorder in a host, including a human, is disclosed that involves administering an effective amount of the compound of Formula (II), administered either alone or in combination with one or more other agents effective in the treatment of an autoimmue disorder.

In another embodiment, a method for the treatment of an inflammatory disease in a host, including a human, is disclosed that involves administering an effective amount of a of the compound of Formula (II), administered either alone or in combination with one or more other anti-inflammatory agents, optionally in a pharmaceutically acceptable carrier, optionally in a pharmaceutically acceptable carrier.

In another embodiment, a method for the treatment of psoriasis in a host, including a human, is disclosed that involves administering an effective amount of the compound of Formula (II), administered either alone or in combination with one or more other anti-psoriasis agents, optionally in a pharmaceutically acceptable carrier.

In another embodiment, a method for the treatment of inflammatory bowel disease in a host, including a human, is disclosed that involves administering an effective amount of the compound of Formula (II), administered either alone or in combination with one or more other anti-inflammatory bowel disease agents, optionally in a pharmaceutically acceptable carrier. In one embodiment, the inflammatory bowel disease is Crohn's disease. In another embodiment, the inflammatory bowel disease is ulcerative colitis.

In another embodiment, a method for the treatment of osteoarthritis in a host, including a human, is disclosed that involves administering an effective amount of the compound of Formula (II), administered either alone or in combination with one or more other anti-osteoarthritis agents, optionally in a pharmaceutically acceptable carrier.

In yet another embodiment, a method for the treatment of chronic obstructive pulmonary disease (COPD) in a host, including a human, is disclosed that involves administering an effective amount of the compound of Formula (II), administered either alone or in combination with one or more other anti-COPD agents, optionally in a pharmaceutically acceptable carrier.

In another embodiment, a method for the treatment of multiple sclerosis (MS) in a host, including a human, is disclosed that involves administering an effective amount of the compound of Formula (II), administered either alone or in combination with one or more other anti-MS agents, optionally in a pharmaceutically acceptable carrier.

The compounds of the present invention can be administered, for example, by parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump administration or via catheter, stent, balloon or other delivery device. In one embodiment, the agent and carrier can be administered in a controlled release formulation such as a monolithic matrix device. In another embodiment, the compounds and compositions described herein can be administered as microcrystalline cellulose tablets. In one particular embodiment, the compounds and compositions described herein can be administered intravenously. In one particular embodiment of the present invention, the compounds and/or compositions described herein can be administered topically. In one embodiment, the compounds and compositions can be administered topically to treat an abnormal cell proliferation disorder, for example, psoriasis. In another particular embodiment, the compounds and/or compositions described herein can be administered topically, for example, as a cream, for the treatment of psoriasis.

DETAILED DESCRIPTION OF THE INVENTION

Disclosed herein is a compound, method and composition for the treatment of abnormal cell proliferation and/or inflammation in a human and other host animals. The method includes administration of an effective anti-proliferative or anti-inflammatory amount of the compounds described herein. The compounds of this invention either posses anti-proliferative and/or anti-inflammatory activity, or are metabolized to a compound that exhibits such activity. In one embodiment of the present invention, the composition and method are used to treat psoriasis. In an alternative embodiment, the composition and method are used to treat inflammatory bowel disease, such as Crohn's disease.

I. Compounds

Figure 1:
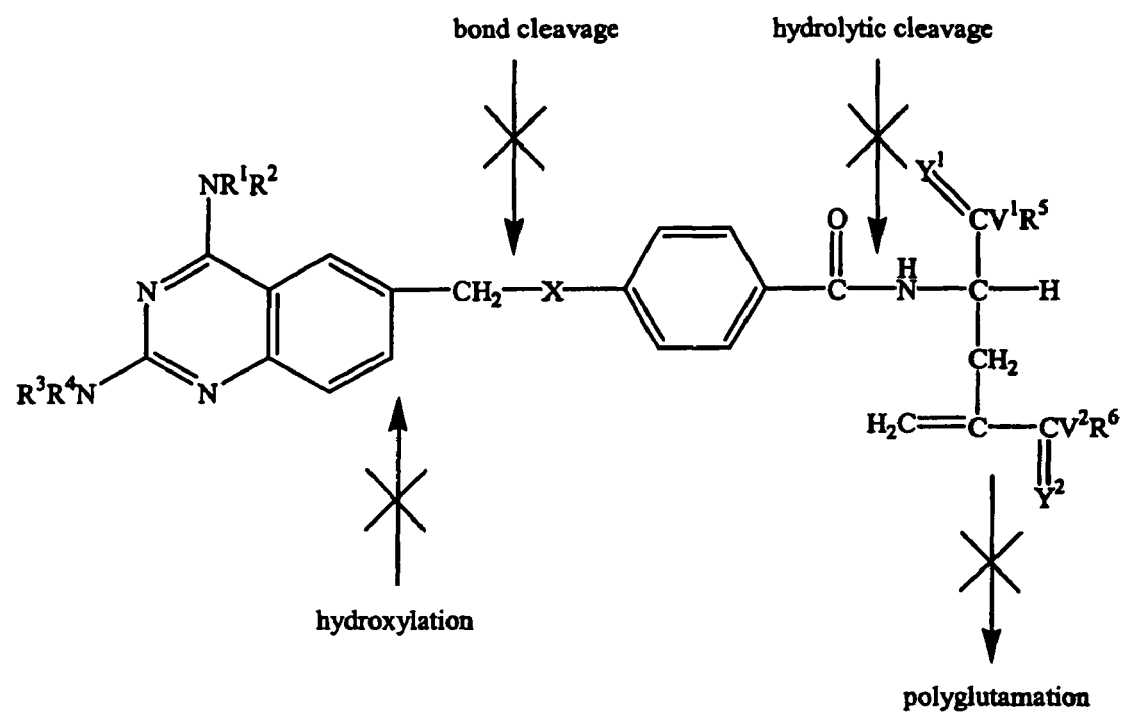
FIG. 1 provides an illustration of the metabolically inert characteristics of the compound of Formula I, as described further below.

The compositions of the present invention are metabolically inert antifolates. The term "metabolically inert antifolate" is intended to include compounds that are (i) folic acid analogs capable of disrupting folate metabolism; (ii) non-polyglutamylatable; and (iii) non-hydroxylatable. A representation of the metabolically inert characteristics of the compounds of the present invention, as illustrated for a particular sub embodiment, is provided in FIG. 1.

Antifolates are compounds that interfere with various stages of foliate metabolism. An intact foliate enzyme pathway is important to maintain de novo synthesis of the building blocks of DNA, as well as of the important amino acids. Antifolate targets include the various enzymes involved in foliate metabolism, including (i) dihydrofolate reductase (DHFR); (ii) thymidylate synthase (TS); (iii) folylpoly-glutamyl synthase; and (iv) glycinamide ribonucleotide (GAR) and aminoimidazole carboxamide ribonucleotide (AICAR) transformylases.

Antifolates are folate acid analogs. For a general review of antifolates, see Montgomery J A and Piper Jr. Design and Synthesis of Folate Analogs as Antimetabolites. In Folate Antagonists as Therapeutic Agents. Volume 1: Biochemistry, Molecular Actions and Synthetic Design. Eds. Sirotnak F M, Burchall J J, Ensminger W D and Montgomery J A. Academic Press. pp 219-261, 1984; Thomas W. *Current Oncology Reports* (2003) 5:114-125; Graffner N M. Approaches to Soft Drug Analogues of Dihydrofolate Reductase Inhibitors, in Comprehensive Summaries of Uppsala Dissertations from the Faculty of Pharmacy 252 (2001); Beale, P., and Clarke, S. Tomudex. Clinical development. In: A. L. Jackman (ed.), Antifolate Drugs in Cancer Therapy, pp. 167-191. Allegra C J: Antifolates, in Chabner B A, Collins J M (eds): Cancer Chemotherapy: Principles & Practice, pp 110-153. Philadelphia, Lippincott, 1990.

Folic acid contains a pteridine ring, para-aminobenzoic acid and a glutamate residue.

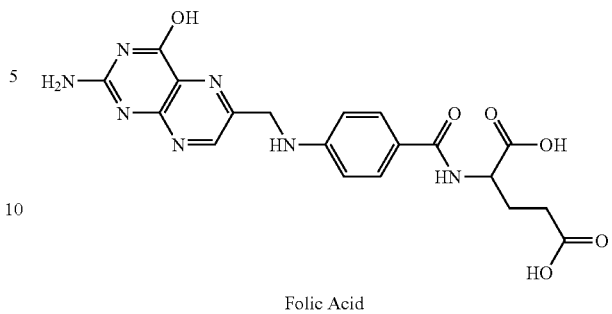

Folic Acid

Methotrexate, a DHFR inhibitor, is among the earliest antifolates. It is a classical antifolate, meaning it is characterized by a p-aminobenzogylglutamic acid side chain, and closely resembles the folic acid molecule. MTX differs from folic acid by the substitution of an amino group for a hydroxyl at the 4-position of the pterdine ring and by the methylation of the amine of the para-aminobenzoic moeity. The substitution of an amino group for a hydroxyl at the 4-position of the pterdine ring changes the enzyme substrate into a tight binding inhibitor of DHFR.

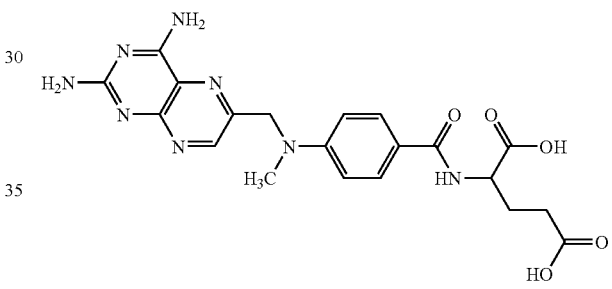

Methotrexate

Both MTX and naturally occurring folate compounds undergo intracellular metabolism to polyglutamate derivatives. This polyglutamylation is catalyzed by the enzyme folylpolyglutamyl synthase (FPGS), which attaches up to six glutamate residues to the molecule, which helps to trap it within the cell. Polyglutamylation of MTX occurs more slowly compared to naturally occurring antifolates, but the resulting methotrexate polyglutamylates have extremely long intracellular half-lives, and can be detected in some tissues more than several months after a single drug administration (Takimoto C H et al. *Oncology* (1995) 9(7): 649-656).

The most common use of MTX is as an anti-cancer drug. MTX is curative of choriocarcinoma and Burkett's lymphoma. It has also widely used as a single agent or in combination with other drugs for the treatment of various forms of human cancer. More recently, MTX has been shown to have anti-inflammatory and immunosuppressive properties with accompanying activity against autoimmune disorders. MTX is now widely prescribed as an immunosuppressive agent in the treatment of autoimmune diseases, including rheumatoid arthritis (Weinblatt M E et al. *N. Ensl. J. Med.* (1985) 312: 818; Wilke W S (Ed). Methotrexate Therapy in Rheumatic Disease. Marcel Dekker, Inc. (1989). Intrinsic and acquired resistance to MTX and other antifolate analogues limits their clinical effectiveness, however. Apart from resistance, major limitations of MTX treatment include bone marrow toxicity, gastrointestinal ulceration and liver and kidney damage.

A number of antifolates have been designed to overcome these limitations. Rational design has focused, for example, on the development of antifolates with greater lipid solubility and/or improved transport characteristics relative to methotrexate (Takimoto C H et al. Oncology (1995) 9(7); 649-656). Representative non-classical agents include trimetrexate and piritrexim (Kamen B A et al. *J. Biochem. Pharmacol.* (1984) 33: 1697-1984; Duch D S et al. *Cancer Res.* (1982) 42: 3987-3994). Unlike classical antifolates, non-classical antifolates lack the glutamate moiety, and therefore do not require carrier-mediated cellular uptake. These lipophilic antifolates are used against opportunistic infections (e.g., *Pneumocystic carinii* pneumonia, PCP) in individuals with AIDS and other disorders of the immune system and have undergone extensive clinical testing as anticancer agents.

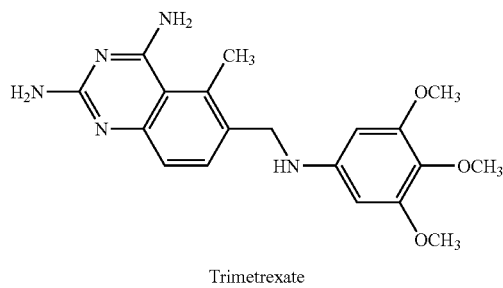

Trimetrexate

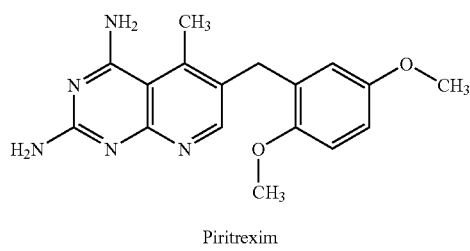

Piritrexim

Other antifolates in clinical development specifically target folate-dependent enzymes such as TS or GARFT, thereby directly affecting pools of nucleotides available for DNA synthesis (Takemura Y. et al. *Anti-Cancer Drugs* (1997) 8: 3-16; Habeck L L et al. *Cancer Res* (1994) 54: 1021-1026). Direct and specific TS inhibitors have been studied as potential anticancer drugs (Stout T J et al. *Biochemistry* (1999) 38: 1607-1617). Of these, Tomudex (raltitrexed; ZD1649), [N-{5-[N-(3-,4-dihydro-2-methyl-4-oxoquinazoline-6-yl-methyl) -N-ylamine]-2-theroyl}-L-glutei acid], is one of the most extensively evaluated and has been approved for treatment in Europe (Van Custom *Euro. J. Cancer*, (1999) 35(Suppl.1): 1-2; Jack man AL. Invest. New Drugs, (1996) 14: 305-316). Comdex undergoes substantial polyglutamylation within the cell. Comdex and its polyglutamates do not appear to inhibit DHFR, GAR or AICAR transformylase, suggesting that the drug is a pure TS inhibitor.

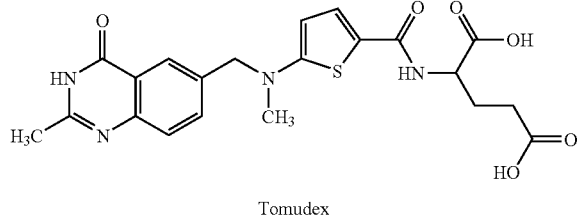

Tomudex

Inhibitors of glycinamide ribotide fonmyltransferase (GARFT) have also been developed. Lometrexol ((5,10-dideazatetrahydrofolate [DDATHF]) is a specific GARFT inhibitor that has shown anti-tumor properties (Habeck L L et al. *Cancer Res*. (1994) 54: 1021-1026). Early clinical trials, however, were confounded by cumulative myelosuppression that prevented repetitive administration (Roberts J D. *Cancer Chemother Pharmacol.* (2000) 45(2):103-10). LY309887 (6R-2',5'-thienyl-5,10-dideazatetrahydrofolic acid) is a thiophene analogue of lometrexol, is a second generation GARFT inhibitor (Mendelsohn L G. *Investig. New Drugs* (1996) 14: 287-294).

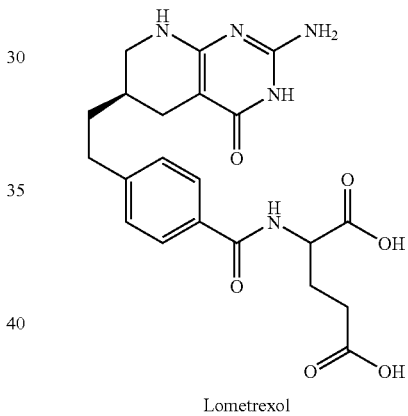

Lometrexol

In 1991, Nair et al. demonstrated that contrary to the widely accepted notion, polyglutamylation of classical antifolates is not essential for anti-tumor activity and further, that this metabolic transformation is actually undesirable because it may cause the loss of pharmacological control and target specificity of the drug (Nair M G et al. *J. Med. Chem* (1991) 34: 222-227). This new finding let to the discovery of a number of nonpolyglutamylatable classical antifolates (Nair M G et al. *Proc. Amer. Assoc. Cancer. Research.* (1998) 39:431).

U.S. Pat. No. 5,073,554 (Nair) describes methylene-1-deazaaminopterine (MDAM), a nonpolyglutamylatable antifolate compound. MDAM has been developed as an experimental anticancer drug for the treatment of human solid tumors (Cao S. et al. *Clinical Cancer Research* (1996) 2(4): 707-712); Johansen M et al. *Cancer Chemother Pharmacol.* (2004) 53(5):370-6). U.S. Pat. No. 5,550,128 (Nair et al) describes the active enantiomer of MDAM as the one possessing the L-configuration.

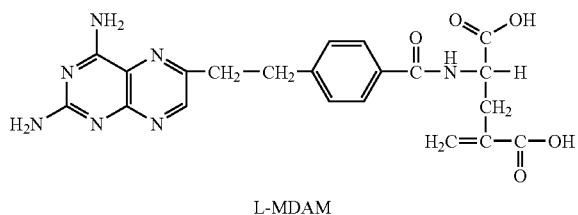

L-MDAM

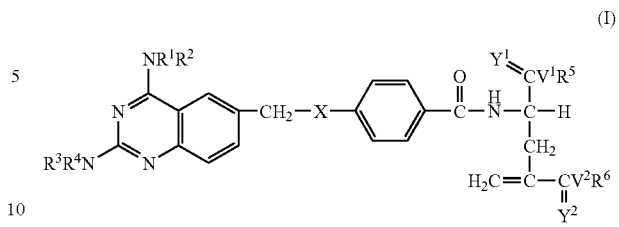

(I)

Further investigation by Nair et al. of the metabolic disposition of certain non-polyglutamylatable antifolates led to the unexpected finding that the presence of the 4-methyleneglutamate moiety modulates the binding of such compounds to the liver enzyme aldehyde oxidase, which mediates their oxidative deactivation to the corresponding 7-hydroxy derivatives (*Cellular. Pharmacology* (1996) 3: 29). U.S. Pat. No. 5,912,251 (Nair) describes metabolically inert classical antifolates, including 4-Amino-4-deoxy-5,8,10-trideazapteroyl-4'-methylene glutamic acid, which are non-polyglutamylatable and non-hydroxylatable. They are said to be useful in the treatment of neoplastic disease (leukemia, ascetic and solid tumors), asthma and related anti-inflammatory disease, and for the treatment of rheumatoid arthritis and other autoimmune diseases.

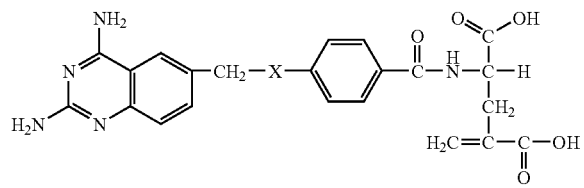

wherein X is $CH_2$, $CHCH_3$, $CH(CH_2CH_3)$, NH, or $NCH_3$.

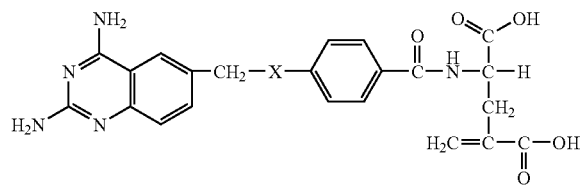

wherein X is $CH_2$.

MTREX

In one embodiment, the compound of Formula (I) is provided as well as a method for the treatment of a host with a disorder characterized by non-neoplastic abnormal cell proliferation, non-asthmatic inflammation including, but not limited to, inflammatory bowel disease (e.g., Crohn's disease) and/or chronic obstructive pulmonary disease (COPD), and/or non-rheumatoid arthritic auto-immune disease including, but not limited to, psoriasis, osteoarthritis, and/or multiple sclerosis (MS), comprising administering an effective treatment amount of compound of Formula (I):

or its pharmaceutically acceptable salt, ester, salt of an ester, amide, salt or an amide, prodrug, salt of a prodrug, or a steroisomeric, tautomeric or polymorphic form thereof; wherein X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —C(=Y)$V^-$ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$;

each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino.

In another embodiment, a method for the treatment of psoriasis in a host, including a human, is disclosed that involves administering an effective amount of the compound of Formula (I), administered either alone or in combination and/or alternation with one or more other anti-psoriasis agent, optionally in a pharmaceutically acceptable carrier.

In another embodiment, a method for the treatment of inflammatory bowel disease in a host, including a human, is disclosed that involves administering an effective amount of the compound of Formula (I), administered either alone or in combination and/or alternation with one or more other anti-inflammatory bowel disease agent, optionally in a pharmaceutically acceptable carrier. In one embodiment, the inflammatory bowel disease is Crohn's disease.

In another preferred embodiment, a method for the treatment of osteoarthritis in a host, including a human, is disclosed that involves administering an effective amount of the compound of Formula (I), administered either alone or in combination and/or alternation with one or more other anti-osteoarthritis agent, optionally in a pharmaceutically acceptable carrier.

In yet another preferred embodiment, a method for the treatment of chronic obstructive pulmonary disease (COPD) in a host, including a human, is disclosed that involves administering an effective amount of the compound of Formula (I), administered either alone or in combination and/or alternation with one or more other anti-COPD agent, optionally in a pharmaceutically acceptable carrier.

In another preferred embodiment, a method for the treatment of multiple sclerosis (MS) in a host, including a human, is disclosed that involves administering an effective amount of the compound of Formula (I), administered either alone or in combination and/or alternation with one or more other anti-MS agent, optionally in a pharmaceutically acceptable carrier.

In an alternative embodiment, the compound of Formula (II) is provided as well as a method for the treatment of a host with a disorder characterized by abnormal cell proliferation, inflammation, and/or auto-immune disease, comprising administering an effective treatment amount of a compound of Formula (II):

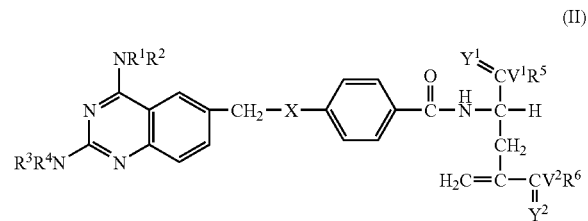

(II)

or its pharmaceutically acceptable salt, ester, salt of an ester, amide, salt or an amide, prodrug, salt of a prodrug, or a steroisomeric, tautomeric or polymorphic form thereof;

wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —C(=Y)V⁻ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino;

such that, if $Y^1$ and $Y^2$ are both oxygen, and $V^1$ and $V^2$ are both oxygen, then at least one of $R^1$, $R^2$, $R^3$, $R^4$, $R^5$, $R^6$, and $R^7$ is not H.

In one particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

X is $NR^7$;

$R^1$, $R^2$, $R^3$, and $R^4$ are independently selected from H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^7$ is independently selected from an optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —C(=Y)V⁻ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino.

In another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

X is $NR^7$ $R^1$, $R^2$, $R^3$, $R^4$ are H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^7$ is independently selected from an optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —$C(=Y)V^{31}$ or —$C(=Y)VH$ moiety when administered in vivo;

each $Y^1$ and $Y^2$ are O each $Y^3$ independently is O, S or $NJ^1$;

each $V^1$ and $V^2$ independently is O;

each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino.

In another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —$C(=Y^3)V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

wherein at least one of $R^1$, $R^2$, $R^3$, $R^4$, and $R^7$ is not H;

$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —$C(=Y)V^{31}$ or —$C(=Y)VH$ moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino.

In yet another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —$C(=Y^3)V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

$R^5$ and $R^6$ are independently selected from H, optionally substituted alkyl including lower alkyl, optionally substituted alkenyl or alkynyl, lipid, phospholipid, carbohydrate, peptide, cholesterol, an amino acid residue or derivative, or other pharmaceutically acceptable leaving group that is capable of providing a —$C(=Y)V^{31}$ . or —$C(=Y)VH$ moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkynyl, aryl, acyl, heteroaromatic, heteroaryl, heteroalkyl, hydroxyl, alkoxy, cyano, azido, halogen, nitro, $SO_2$, $SO_3$, thioalkyl, or amino;

such that, if $Y^1$ and $Y^2$ are both oxygen, and $V^1$ and $V^2$ are both oxygen, then at least one of $R^1$, $R^2$, $R^3$, $R^4$, $R^5$, $R^6$, and $R^7$ is not H.

In yet another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

at least one of $R^1$, $R^2$, $R^3$, $R^4$, and $R^7$ is selected from an optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, lipid, phospholipid, carbohydrate, peptide, cholesterol, an amino acid residue or derivative, an amino acid acyl residue or derivative or other pharmaceutically acceptable leaving group that is capable of providing a free amine when administered in vivo;

each $Y^1$ and $Y^2$ is O; and each $V^1$ and $V^2$ is O.

In another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

at least one of $R^1$, $R^2$, $R^3$, $R^4$, and $R^7$ is selected from an optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), —C(=$Y^3$)$V^3$, an amino acid residue or derivative, or an amino acid acyl residue or derivative;

each $Y^1$ and $Y^2$ is O; and each $V^1$ and $V^2$ is O.

In another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

at least one of $R^1$, $R^2$, $R^3$, $R^4$, and $R^7$ is selected from an optionally acyl, —C(O)-(alkyl), —C(O)(lower alkyl), —C(O)-(alkenyl), —C(O)-(alkynyl), —C(=$Y^3$)$V^3$, or an amino acid acyl residue or derivative;

each $Y^1$ and $Y^2$ is O; and each $V^1$ and $V^2$ is O.

In yet another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

at least one of $R^5$ and $R^6$ is selected from an optionally substituted alkyl including lower alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)V or —C(=Y)VH moiety when administered in vivo;

each $Y^1$ and $Y^2$ is O; and each V and $V^2$ is O.

In another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

at least one of $R^5$ and $R^6$ is selected from an optionally substituted alkyl including lower alkyl, optionally substituted alkenyl or alkenyl, or an amino acid residue or derivative, or other pharmaceutically acceptable leaving group that is capable of providing a —C(=Y)V⁻ or —C(=Y)VH moiety when administered in vivo;

each $Y^1$ and $Y^2$ is O; and each $V^1$ and $V^2$ is O.

In another particular embodiment of the present invention, the compound of Formula (II) is provided as well as a method for the treatment of a host with a disorder characterized by abnormal cell proliferation, inflammation, and/or auto-immune disease, comprising administering an effective treatment amount of the compound of Formula (II) wherein:

at least one of $R^5$ and $R^6$ is selected from an optionally substituted alkyl including lower alkyl, optionally substituted alkenyl or alkenyl, or an amino acid residue or derivative;

each $Y^1$ and $Y^2$ is O; and each $V^1$ and $V^2$ is O.

In one embodiment, a method for the treatment of abnormal cell proliferation in a host, including a human, is disclosed that involves administering an effective amount of the compound of Formula (II), administered either alone or in combination and/or alternation with one or more other anti-abnormal cell proliferation agent, optionally in a pharmaceutically acceptable carrier.

In one embodiment, a method for the treatment of abnormal cell proliferation in a host, including a human, is disclosed that involves administering an effective amount of the compound of Formula (II), administered either alone or in combination and/or alternation with one or more other agent effective in the treatment of an autoimmue disorder.

In another embodiment, a method for the treatment of an inflammatory disease in a host, including a human, is disclosed that involves administering an effective amount of a of the compound of Formula (II), administered either alone or in combination and/or alternation with one or more other anti-inflammatory agent, optionally in a pharmaceutically acceptable carrier, optionally in a pharmaceutically acceptable carrier.

In another embodiment, a method for the treatment of psoriasis in a host, including a human, is disclosed that involves administering an effective amount of the compound of Formula (II), administered either alone or in combination and/or alternation with one or more other anti-psoriasis agent, optionally in a pharmaceutically acceptable carrier.

In another embodiment, a method for the treatment of inflammatory bowel disease in a host, including a human, is disclosed that involves administering an effective amount of the compound of Formula (II), administered either alone or in combination and/or alternation with one or more other anti-inflammatory bowel disease agent, optionally in a pharmaceutically acceptable carrier. In one embodiment, the inflammatory bowel disease is Crohn's disease.

In another preferred embodiment, a method for the treatment of osteoarthritis in a host, including a human, is disclosed that involves administering an effective amount of the compound of Formula (II), administered either alone or in combination and/or alternation with one or more other anti-osteoarthritis agent, optionally in a pharmaceutically acceptable carrier.

In yet another preferred embodiment, a method for the treatment of chronic obstructive pulmonary disease (COPD) in a host, including a human, is disclosed that involves administering an effective amount of the compound of Formula (II), administered either alone or in combination and/or alternation with one or more other anti-COPD agent, optionally in a pharmaceutically acceptable carrier.

In another preferred embodiment, a method for the treatment of multiple sclerosis (MS) in a host, including a human, is disclosed that involves administering an effective amount of the compound of Formula (II), administered either alone or in combination and/or alternation with one or more other anti-MS agent, optionally in a pharmaceutically acceptable carrier.

Other particular embodiments include:

A compound of the formula:

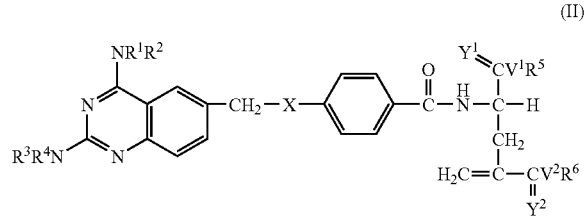

(II)

or its pharmaceutically acceptable salt, wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a C(=Y)$V^{31}$ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101\ R102}$, or $CR^{101}R^{102}R^{103}$;

each $J^1$, $J^2$ and $J^3$ independently are hydrogen, alkyl, alkenyl, alkenyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino;

such that, if $Y^1$ and $Y^2$ are both oxygen, and $V^1$ and $V^2$ are both oxygen, then at least one of $R^1$, $^2$, $R^3$, $R^4$, $R^5$, $R^6$, and $R^7$ is not H.

A method for the treatment of abnormal cell proliferation, comprising administering an effective amount of a compound of the formula below in combination with an anti-neoplastic agent:

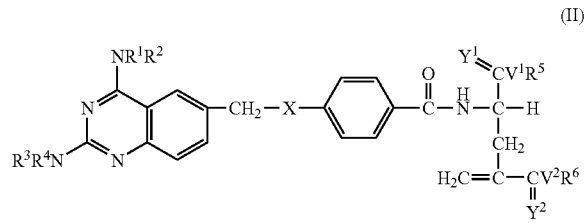

(II)

or its pharmaceutically acceptable salt, wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)$V^{31}$ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkenyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino;

A method to treat a disease or disorder characterized by abnormal cell proliferation in a host, comprising administering an effective amount of the compound of Formula (II).

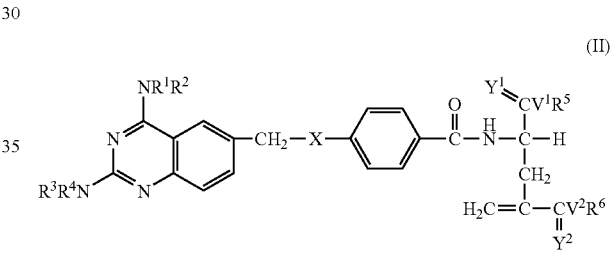

(II)

or its pharmaceutically acceptable salt; wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)$V^{31}$ or —C(=Y)VH moiety when administered in vivo;

each $Y^1$, $Y^2$, and Y independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{102}$;

each $J^1$, $J^2$ and $J^3$ independently are hydrogen, alkyl, alkenyl, alkenyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino;

such that, when the disorder is a tumor, if $Y^1$ and $Y^2$ are both oxygen, and $V^1$ and $V^2$ are both oxygen, then at least one of $R^1$, $R^2$, $R^3$, $R^4$, $R^5$, $R^6$, and $R^7$ is not H.

A method to treat an inflammatory disease or disorder in a host, comprising administering an effective amount of the compound of Formula (II).

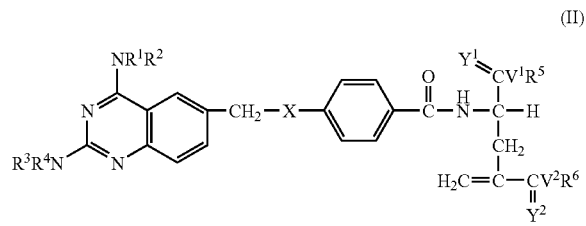

or its pharmaceutically acceptable salt; wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)$V^{31}$ or C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ_1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkenyl, alkaryl, cycloalkyl, aryl, cycloaryl, heterbalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino;

such that, if $Y^1$ and $Y^2$ are both oxygen, and $V^1$ and $V^2$ are both oxygen, then at least one of $R^1$, $R^2$, $R^3$, $R^4$, $R^5$, $R^6$, and $R^7$ is not H.

A method to treat an autoimmune disease or disorder in a host, comprising administering an effective amount of the compound of Formula (II)

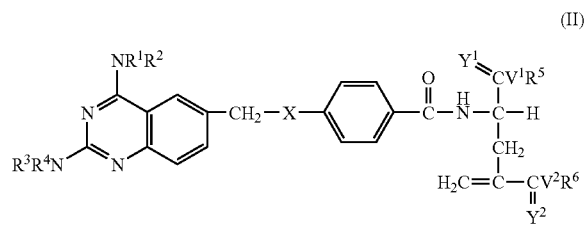

or its pharmaceutically acceptable salt; wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)$V^{31}$ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$ or $CR^{101}R^{102}R^{103}$;

each $J^1$, $J^2$ and $J^3$ independently are hydrogen, alkyl, alkenyl, alkenyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino;

such that, if $Y^1$ and $Y^2$ are both oxygen, and $V^1$ and $V^2$ are both oxygen, then at least one of $R^1$, $R^2$, $R^3$, $R^4$, $R^5$, $R^6$, and $R^7$ is not H.

A method of treating psoriasis, comprising administering an effective amount of the compound of Formula (I):

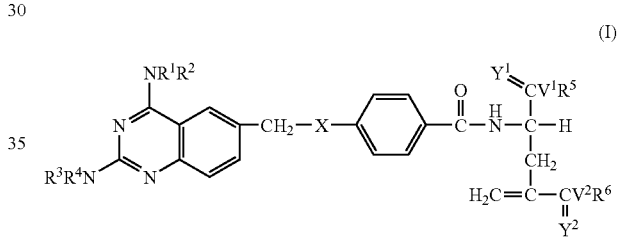

or its pharmaceutically acceptable salt; wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)$V^{31}$ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkenyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino.

A method of treating inflammatory bowel disease, comprising administering an effective amount of the compound of Formula (I):

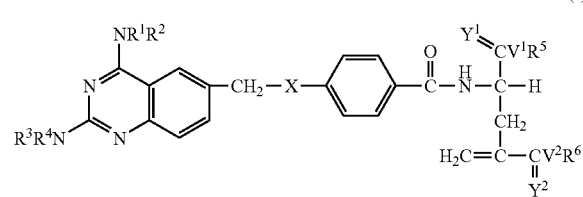

or its pharmaceutically acceptable salt; wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=Y$^3$)V$^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)V$^{31}$ or —C(=Y)VH moiety when administered in vivo;

each $Y^1$, $Y^2$ and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkenyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino;

A method of treating multiple sclerosis in a host, comprising administering an effective amount of the compound of Formula (I):

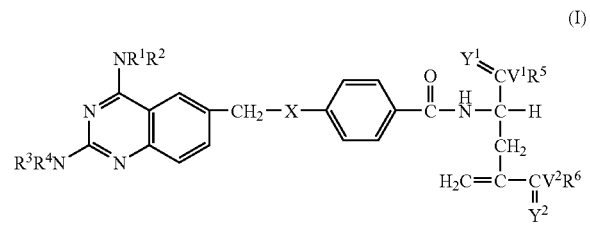

or its pharmaceutically acceptable salt; wherein

X is $CH_2$, $CHCH_3$, $CH(CH_2CH_3)$, NH, $NCH_3$, or $NR^7$ $R^1$, $R^2$, $R^3$, $R^4$, and $R^7$ are independently selected from H, optionally substituted alkyl, optionally substituted alkenyl or alkenyl, acyl, —C(O)-(alkyl), —C(O)-(alkenyl), —C(O)-(alkynyl), —C(=Y$^3$)V$^3$, lipid, phospholipid, carbohydrate, peptide, cholesterol, an amino acid residue or an amino acid acyl residue;

$R^5$ and $R^6$ are independently selected from H, optionally substituted alkyl, optionally substituted alkenyl or alkenyl, lipid, phospholipid, carbohydrate, peptide, cholesterol, an amino acid residue or derivative, or other pharmaceutically acceptable leaving group that is capable of providing a —C(=Y)V$^{31}$ or —C(=Y)VH moiety when administered in vivo;

each $Y^1$, $Y^2$, and $Y^3$ independently is O, S or $NJ^1$;

each $V^1$ and $V^2$ independently is O, S or $NJ^1$ each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$, $J^2$ and $J^3$ independently are hydrogen, alkyl, alkenyl, alkenyl, alkaryl, cycloalkyl, aryl, cycloaryl, heteroalkyl, heterocycle, heteroaryl, hydroxyl, alkoxy, or amine; and each $R^{100}$, $R^{101}$, $R^{102}$, and $R^{103}$ are independently hydrogen, alkyl, alkenyl, alkenyl, aryl, acyl, heteroaromatic, heteroaryl, heteroalkyl, hydroxyl, alkoxy, cyano, azido, halogen, nitro, $SO_2$, $SO_3$, thioalkyl, or amino;

such that, if $Y^1$ and $Y^2$ are both oxygen, and $V^1$ and $V^2$ are both oxygen, then at least one of $R^1$, $R^2$, $R^3$, $R^4$, $R^5$, $R^6$, and $R^7$ is not H.

A pharmaceutically acceptable salt of a compound of the formula:

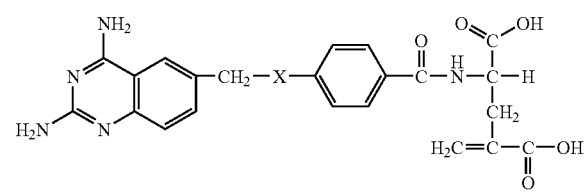

wherein X is $CH_2$, $CHCH_3$, $CH(CH_2CH_3)$, NH, or $NCH_3$.

II. Definitions

The term "alkyl" as used herein, unless otherwise specified, refers to a saturated straight, branched, or cyclic, primary, secondary, or tertiary hydrocarbon of, for example, $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstantiated alkyl groups. Moieties with which the alkyl group can be substituted with one or more substituents are selected from the group consisting of halo, including Cl, F, Br and I so as to form, for e.g., $CF_3$, 2-Br-ethyl, $CH_2F$, $CH_2Cl$, $CH_2CF_3$, or $CF_2CF_3$; hydroxyl, for e.g. $CH_2OH$; amino, for eg., $CH_2NH_2$, $CH_2NHCH_3$, or $CH_2N(CH_3)_2$; carboxylate; carboxamido; alkylamino; arylamino; alkoxy; aryloxy; nitro; azido, for eg., $CH_2N_3$; cyano, for eg., $CH_2CN$; thio; sulfonic acid; sulfate; phosphonic acid; phosphate; and phosphonate, either unprotected or protected as necessary, known to those skilled in the art, for eg., as taught in Greene et al., *Protective Groups in Organic Synthesis*, John Wiley and Sons, Second Edition (1991), incorporated herein by reference.

The term "lower alkyl", as used herein, and unless otherwise specified, refers to a $C_1$ to $C_6$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms alkenyl and alkynyl refer to alkyl moieties wherein at least one saturated C—C bond is replaced by a double or triple bond. Thus, $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, or 5-hexynyl.

As used herein, with exceptions as noted, "aryl" is intended to mean any stable monocyclic, bicyclic or tricyclic carbon ring of up to 8 members in each ring, wherein at least one ring is aromatic as defined by the Huckel 4n+2 rule. Examples of aryl ring systems include phenyl, naphthyl, tetrahydronaphthyl, and biphenyl. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis* John Wiley and Sons, Second Edition, 1991.

The terms "aralkyl" and "arylalkyl", as used herein, and unless otherwise specified, refers to an aryl group as defined above linked to the molecule through an alkyl group as defined above.

The term "alkaryl" and "alkylaryl", as used herein, and unless otherwise specified, refers to an alkyl group as defined above linked to the molecule through an aryl group as defined above.

The term alkoxy, as used herein, and unless otherwise specified, refers to a moiety of the structure —O-alkyl, wherein alkyl is as defined above.

The term "halo" as used herein includes bromo, chloro, iodo and fluoro.

The term "acyl" refers to a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, $C_1-C_6$ alkyl or $C_1-C_6$ alkoxy; sulfonate esters such as alkyl or aralkyl sulphonyl including methanesulfonyl; the mono-, di- or triphosphate ester; trityl or monomethoxytrityl; substituted benzyl; trialkylsilyl as, for e.g., dimethyl-t-butylsilyl or diphenylmethylsilyl. Aryl groups in the esters optimally comprise a phenyl group.

The term "lower acyl" refers to an acyl group in which the non-carbonyl moiety is lower alkyl.

The term amino, as used herein, refers to a moiety represented by the structure $-NR_2$, and includes primary amines, and secondary, and tertiary amines substituted by alkyl (i.e. alkylamino). Thus, $R_2$ may represent two hydrogens, two alkyl moieties, or one hydrogen and one alkyl moiety.

The terms "alkylamino" and "arylamino" refer to an amino group that has one or two alkyl or aryl substituents, respectively.

The term "protected" as used herein and, unless otherwise defined, refers to a group that is added to an oxygen, nitrogen or phosphorus atom to prevent its further reaction or for other purposes. Numerous oxygen and nitrogen protecting groups are known to those skilled in the art of organic synthesis.

The term amido, as used herein, refers to a moiety represented by the structure —$C(O)NR_2$, wherein $R_2$ is as defined for amino.

As used herein, an "amino acid" is a natural amino acid residue (e.g. Ala, Arg, Asn, Asp, Cys, Glu, Gln, Gly, His, Hyl, Hyp, Ile, Leu Lys, Met, Phe, Pro, Ser, Thr, Trp, Tyr, and Val) in D or L form, or an unnatural amino acid (e.g. phosphoserine; phosphothreonine; phosphotyrosine; gamma-carboxyglutamate; hippuric acid; octahydroindole-2-carboxylic acid; statine; 1,2,3,4,-tetrahydroisoquinoline-3-carboxylic acid; penicillamine; ornithine; citrulline; α-methyl-alanine; para-benzoylphenylalanine; phenylglycine; propargyl-glycine; sarcosine; and tert-butylglycine) residue having one or more open valences. Other unnatural amino acids include those represented by the formula $NH_2$ $(CH_2)_y$ COOH, wherein y=2-20, and preferably 2-12, and include the aminoalkanoic acids such as ε-amino caproic acid $(H_2N—(CH_2)_5—COOH)$.

The term also comprises natural and unnatural amino acids bearing amino protecting groups such as acetyl, acyl, trifluoroacetyl, and benzyloxycarbonyl), as well as natural and unnatural amino acids protected at carboxy with protecting groups such as a $C_1-C_6$ alkyl, phenyl or benzyl ester and amide. Other suitable amino and carboxy protecting groups are known to those skilled in the art. See for example, T. W. Greene, *Protecting Groups in Organic Synthesis*; Wiley: New York, 1981; D. Voet, Biochemistry, Wiley: New York, 1990; L. Stryer, *Biochemistry*, ($3^{rd}$ Ed), W. H. Freeman and Co.: New York, 1975; J. March, *Advanced Organic Chemistry. Reactions, Mechanisms and Structure*, ($2^{nd}$ Ed.), McGraw Hill: New York, 1977; F. Carey and R. Sundberg, *Advanced Organic Chemistry. Part B: Reactions and Synthesis, ($2^{nd}$ Ed.)*, Plenum: New York, 1977; and references cited therein.

The term heteroalkyl refers to an alkyl group that contains a heteroatom in the alkyl chain, including O, S, N, or P, and wherein the heteroatom can be attached to other substituents to complete the valence. Non-limiting examples of heteralkyl moieties include polyoxyalkylene, and when divalent, $—(CH_2O)_n—$ wherein n is an integer of from 0 to 20.

The term heterocycle or heterocyclic, as used herein except where noted represents a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S; and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

The term heteroaryl or heteroaromatic, as used herein, refers to an aromatic moiety that includes at least one sulfur, oxygen, nitrogen or phosphorus in the aromatic ring. The term heterocyclic refers to a nonaromatic cyclic group wherein there is at least one heteroatom, such as oxygen, sulfur, nitrogen, or phosphorus in the ring. Non-limiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrimidine, uracil, $N^5$-alkyl-pyrimidines, $N^5$-benzylpyrimidines, $N^5$-halopyrimidines, $N^5$-vinyl-pyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic and heterocyclic moieties can be optionally substituted as described above for aryl, including substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, t-butyldi-methylsilyl, and t-butyldiphenylsilyl, trityl or substituted trityl, alkyl groups, acyl groups such as acetyl and propionyl, methanesulfonyl, and p-toluenesulfonyl.

As used herein, the terms "substantially free of" and "substantially in the absence of" refer to a composition that includes at least 85-90% by weight, preferably 95%-98% by weight, and even more preferably 99%-100% by weight, of the designated enantiomer of that compound. In a preferred embodiment, the compounds listed in the methods and compounds of this invention are substantially free of enantiomers other than for the one designated.

Similarly, the term "isolated" refers to a composition that includes at least 85%-90% by weight, preferably 95%-98% by weight, and even more preferably 99%-100% by weight, of the compound, the remainder comprising other chemical species or enantiomers.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

The term "host", as used herein, refers to unicellular or multicellular organism in which abnormal cellular proliferation can be mimicked. The term host specifically refers to cells that abnormally proliferate, either from natural or unnatural causes (for example, from genetic mutation or genetic engineering, respectively), and animals, in particular, primates (including chimpanzees) and humans. In most animal applications of the present invention, the host is a human patient. Veterinary applications, in certain indications, however, are clearly anticipated by the present invention.

III Prodrugs and Derivatives

The active compound can be administered as any salt or prodrug that upon administration to the recipient is capable of providing directly or indirectly the parent. compound, or that exhibits activity itself.

A. Pharmaceutically Acceptable Salts

In cases where compounds are sufficiently basic or acidic to form stable nontoxic acid or base salts, administration of the compound as a pharmaceutically acceptable salt may be appropriate.

The term "pharmaceutically acceptable salt" refers to a salt or complex of the active compound in which the compound carries a counterion that is pharmaceutically acceptable and retains the desired biological activity of the parent compound and exhibits minimal, if any, undesired toxicological effects. Any salt that retains the desired biological activity of the compounds contained herein and that exhibits minimal or no undesired or toxicological effects is intended for inclusion here.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, bicarbonic acid, carbonic acid and the like), and salts formed with organic acids such as acetic acid, oxalic acid, formic acid, fumaric acid, propionic acid, glycolic acid, lactic acid, pyruvic acid, maleic acid, salicylic acid, tartaric acid, succinic acid, malic acid, ascorbic acid, benzoic acid, tannic acid, palmoic acid, alginic acid, polyglutamic acid, tosic acid, methanesulphonic acid, citric acid, malonic acid, α-ketoglutaric acid, α-glycerophosphonic acid, naphthalenesulfonic acids, naphthalene-disulfonic acids, and polygalacturonic acid; (b) base addition salts formed with cations such as sodium, potassium, lithium, zinc, calcium, bismuth, barium, magnesium, aluminum, copper, cobalt, nickel, cadmium, and the like, or with an organic cation, for example, formed from an amine, such as ammonium, N,N-dibenzyl-ethylenediamine, D-glucosamine, tetraethylammonium, or ethylenediamine; or (c) combinations of (a) and (b), e.g., a zinc tannate salt or the like.

B. Prodrugs

Any of the compounds described herein can be administered as a prodrug to increase the activity, bioavailability, stability or otherwise alter the properties of the compound. A pharmaceutically acceptable prodrug refers to a compound that is metabolized (i.e., hydrolyzed or oxidized, for example) in the host to form a compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The compounds of this invention possess anti-proliferative activity against abnormally proliferating cells, or are metabolized to a compound that exhibits such activity.

A number of prodrug ligands are known. In general, alkylation, acylation or other lipophilic modification of one or more heteroatoms of the compound, such as a free amine or carboxylic acid residue, reduces polarity and allows passage into cells. Examples of substituent groups that can replace one or more hydrogens on the free amine and/or carboxylic acid moiety are alkyl, aryl, steroids, carbohydrates, including sugars, 1,2-diacylglycerol, alcohols, acyl (including lower acyl); alkyl (including lower alkyl); sulfonate ester including alkyl or arylalkyl sulfonyl including methanesulfonyl and benzyl, wherein the phenyl group is optionally substituted with one or more substituents as provided in the definition of an aryl given herein; optionally substituted arylsulfonyl; a lipid, including a phospholipid; phosphotidylcholine, phosphocholine, an amino acid residue or derivative; an amino acid acyl residue or derivative; a carbohydrate; a peptide; cholesterol; or other pharmaceutically acceptable leaving group which, when administered in vivo, provides the free amine and/or carboxylic acid moiety. Any of these can be used in combination with the disclosed compounds to achieve a desired effect.

C. Stereochemistry

It is to be understood that the compounds disclosed herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the disclosure of a compound herein encompasses any racemic, optically active, polymorphic, or steroisomeric form, or mixtures thereof, which preferably possesses the useful properties described herein, it being well known in the art how to prepare optically active forms and how to determine activity using the standard tests described herein, or using other similar tests which are will known in the art. Examples of methods that can be used to obtain optical isomers of the compounds include the following:

i) physical separation of crystals— a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization— a technique whereby the individual enantiomers are separately crystallized from a solution of the racemate, possible only if the latter is a conglomerate in the solid state;

iii) enzymatic resolutions— a technique whereby partial or complete separation of a racemate by virtue of differing rates of reaction for the enantiomers with an enzyme iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis— a synthetic technique whereby the desired enantiomer is synthesized from an achiral precursor under conditions that produce asymetry (i.e., chirality) in the product, which may be achieved using chiral catalysts or chiral auxiliaries;

vi) diastereomer separations— a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first— and second-order asymmetric transformations a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer, viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography, a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography, a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent; and xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, e.g., a mixture of enantiomers in which one enantiomer is present in excess, e.g., to the extent of 95% or more, or 98% or more, including 100%.

IV. Synthesis

Figure 2:
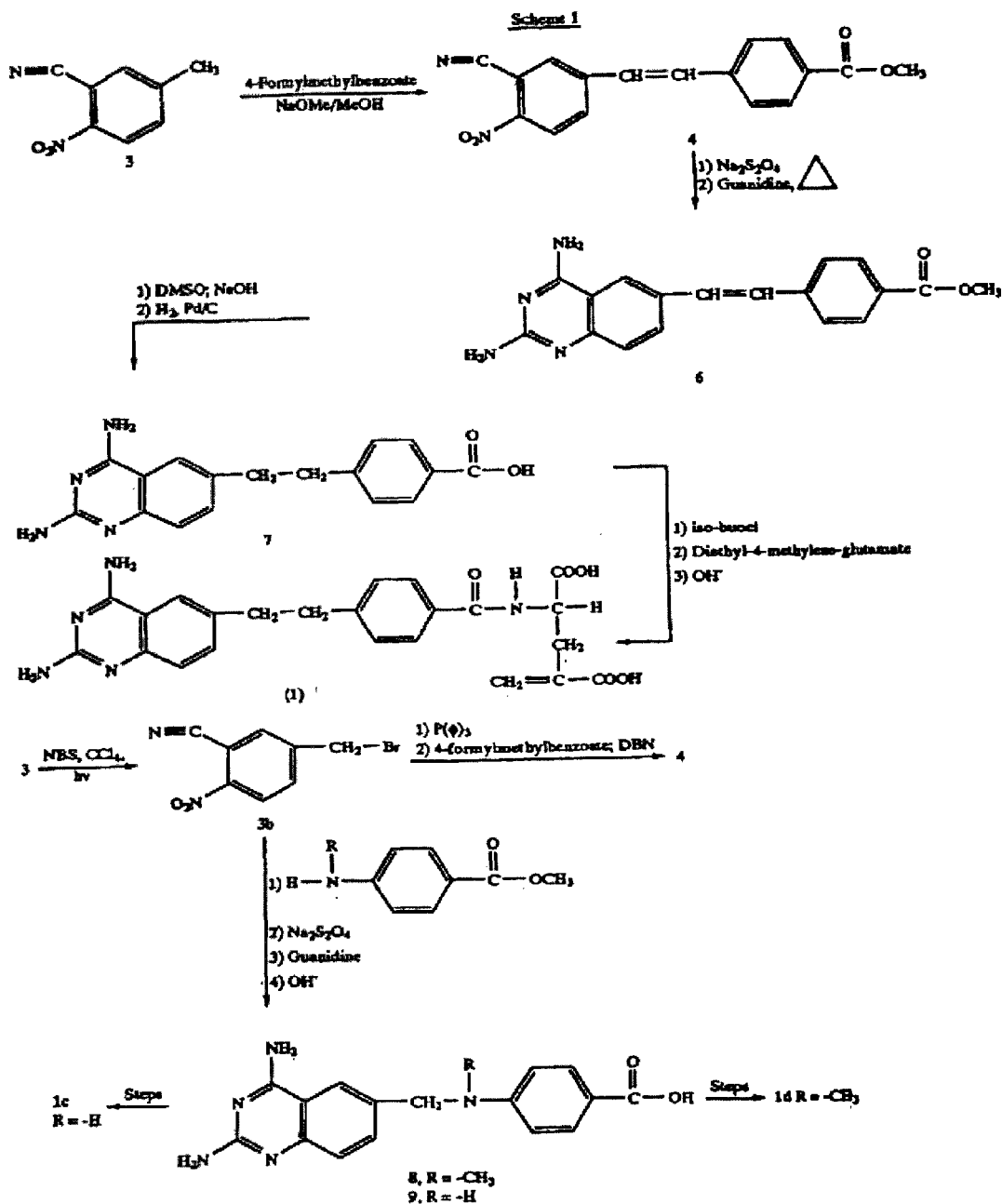
FIG. 2 provides an illustration of the synthesis of a sub-embodiment of the compound of Formula I, as described further below.

As depicted in FIG. 2, the process of the invention for the synthesis of a sub-embodiment of the compound of Formula (I) starts with the conversion of commercially available 5-methyl-2-nitrobenzoic acid to the corresponding amide (2) and its subsequent transformation to 5-methyl-2-nitrobenzonitrile (3) by standard procedures. Reaction of (3) in DMF under nitrogen with p-formylmethylbenzoate in the presence of an organic base such as diazabicylo octane for several hours gave the olefin (4) after work up as a mixture of geometric isomers. Olefin (4) can also be prepared by reacting (3) with p-formylmethylbenzoate in methanol using sodium methoxide as a base. In general, this reaction can be performed in any appropriate organic solvent using commonly used organic or inorganic bases. Reduction of (4) with a reducing agent, such as sodium dithionite, gave the aminonitrile (5), which was cyclized with guanidine to the corresponding pteroate analogue (6), which after catalytic hydrogenation and hydrolysis gave 4-amino-4-deoxy-5,8,10-trideazapteroic acid (7). Coupling of (7) with diethyl-4-methyleneglutamate by the isobutylchlorformate method previously described by Nair and Baugh [Biochemistry (1973) 12: 3923-3927] followed by mild hydrolysis of the resultant diester gave crude (1) which was purified by reverse phase chromatography on C-18 silica gel using 12% acetonitrile in water as the eluting solvent [Scheme-1].

An alternate procedure for the preparation of olefin (4) is allylic bromination of (3) to the corresponding benzyl bromide (3b), and its subsequent reaction with triphenylphosphine to the Wittig salt. Treatment of this Wittig salt with p-formylmethylbenzoate in an organic solvent (e.g., DMF) using an organic base in a typical Wittig reaction gave (4) in moderate yield. Any convenient organic solvent and an organic or inorganic base compatible with the solvent can be used for this reaction.

Substitution of p-formyl methylbenzoate with p-carbomethoxyacetophenone in the above reaction with (3) gives the corresponding methyl substituted olefin which after dithionite reduction, guanidine cyclization, hydrogenation, hydrolysis, diethyl-4-methyleneglutamate coupling followed by hydrolysis yields the 10-methyl derivative (1a). Likewise, substitution of p-formyl methylbenzoate with p-carbomethoxy-propiophenone in the reaction with (3) and workup as above should yield the 10-ethyl derivative (1b).

Benzylic bromination of (3) gave the corresponding bromomethyl derivative (3b) that on reaction with p-methylaminomethybenzoate an dmethyl-p-methylaminobenzoate gave the corresponding aminonitriles which after dithionite reduction, guanidine cyclization and hydrolysis gave the pteroate analogs (3) and (9). 4-Methyleneglutamate coupling described as above and hydrolysis gave the 10-nor-methylamino and 10-nor-amino derivatives (1c) and (1d), respectively.

V. Pharmaceutical Compositions and Administration

Any host organism, including a patient, mammal, and specifically a human, suffering from any of the above-described conditions can be treated by the administration of a composition comprising an effective amount of the compound of formula (I) or formula (II) or a pharmaceutically acceptable salt, prodrug or ester thereof, optionally in a pharmaceutically acceptable carrier. The term "carrier" includes but is not limited to diluents, binders, lubricants, disintegrators, fillers, and coating compositions.

An effective dose for any of the herein described conditions can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects. The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

The compound can also be mixed with other active materials that do not impair the desired action, or with materials that supplement the desired action. For a detailed description, see, for example, Section VII, "Combination Therapies."

The formulations of the pharmaceutical compositions described herein may be prepared by any method known or hereafter developed in the art of pharmacology. In general, such preparatory methods include the step of bringing the therapeutic compound into association with a carrier or one or more other accessory ingredients, and then, if necessary or desirable, shaping or packaging the product into a desired single- or multi-dose unit.

In one embodiment, compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. For the purpose of oral therapeutic administration, the compound can be incorporated with one or more excipients and used in the form of tablets, buccal tablets, troches, capsules, elixirs, suspensions, syrups, wafers and the like. The percentage of the composition and preparations may be varied, and may conveniently be between from about 2% to about 60% of the weight of a given unit dosage form. The amount of substance in such therapeutically useful compositions is such that an effective dosage level will be obtained.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. In one particular embodiment, the compounds and compositions disclosed herein can be formulated as microcrystalline cellulose tablets.

Hard capsules containing the compound may be made using a physiologically degradable composition, such as gelatin. Such hard capsules comprise the compound, and may further comprise additional ingredients including, for example, an inert solid diluent such as calcium carbonate, calcium phosphate, or kaolin. Soft gelatin capsules containing the compound may be made using a physiologically degradable composition, such as gelatin. Such soft capsules comprise the compound, which may be mixed with water or an oil medium such as peanut oil, liquid paraffin, or olive oil.

Sublingual tablets are designed to dissolve very rapidly. Examples of such formulations include ergotamine tartrate, isosorbide dinitrate, isoproterenol HCL. The formulations of these tablets contain, in addition to the drug, a limited number of soluble excipients, usually lactose and powdered sucrose, but sometimes dextrose and mannitol.

The solid dosage forms of the present invention may optionally be coated. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit.RTM. (Roth Pharma, Westerstadt, Germany), Zein, shellac, and polysaccharides.

Powdered and granular formulations of a pharmaceutical preparation of the invention may be prepared using known methods. Such formulations may be administered directly to a patient used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative.

Additional excipients (e.g., fillers and sweetening, flavoring, or coloring agents) may also be included in these formulations.

Liquid formulations of the pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the compound and an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may also contain one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Suspending agents may include, for example, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Dispersing or wetting agents may include, for example, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Emulsifying agents include, but are not limited to, lecithin and acacia. Preservatives may include, for example, methyl, ethyl, or n-propyl-para-hydroxybenzoates, ascorbic acid, and sorbic acid. Sweetening agents include, for example, glycerol, propylene glycol, sorbitol, sucrose, and saccharin. Thickening agents for oily suspensions include, for example, beeswax, hard paraffin, and acetyl alcohol.

Liquid solutions of the active ingredient in aqueous or oily solvents may be prepared in substantially the same manner as liquid suspensions, wherein the active ingredient is dissolved, rather than suspended in the solvent. Liquid solutions of the pharmaceutical composition of the invention may contain each of the components described above for liquid suspensions, other than suspending agents, which are unnecessary. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Administration

The compositions can be administered in any desired manner, including, but not limited to, oral, topical, parenteral, intravenous, intradermal, intra-articular, intra-synovial, intrathecal, intra-arterial, intracardiac, intramuscular, subcutaneous, intraorbital, intracapsular, intraspinal, intrastemal, topical, transdermal patch, via rectal, vaginal or urethral suppository, peritoneal, percutaneous, nasal spray, surgical implant, internal surgical paint, infusion pump, or via catheter, stent, balloon or other delivery device.

Parenteral administration of the pharmaceutical composition includes any route of administration characterized by physical breaching of a tissue of a subject and administration of the pharmaceutical composition through the breach in the tissue, such as administration of the pharmaceutical composition by injection of the composition, by application of the composition through a surgical incision, by application of the composition through a tissue-penetrating non-surgical wound, and the like.

Formulations of a pharmaceutical composition suitable for parenteral administration comprise the compound combined with a pharmaceutically acceptable carrier, such as sterile water or sterile isotonic saline. Formulations suitable for parenteral administration include, for example, suspensions, solutions, emulsions in oily or aqueous vehicles. Such formulations may further comprise one or more additional ingredients including, but not limited to, suspending, stabilizing, or dispersing agents. In one embodiment of a formulation for parenteral administration, the compound is provided in dry (i.e., powder or granular) form for reconstitution with a suitable vehicle (e.g., sterile pyrogen-free water) prior to parenteral administration of the reconstituted composition.

In one embodiment, the compound administered intravenously or intraperitoneally by infusion or injection. The pharmaceutical dosage forms suitable for infusion or injection can include sterile aqueous solutions or dispersions or sterile powders containing the substance which are adapted for the extemporaneous preparation of sterile injectable or infusible solutions or dispersions, optionally encapsulated in liposomes. In all cases, the ultimate dosage form must be sterile, fluid and stable under the conditions of storage or manufacture. The liquid carrier or vehicle can be a solvent or liquid dispersion medium comprising, for example, water, normal saline, ethanol, a polyol (e.g.; glycerol, propylene glycol, liquid polyethylene glycol and the like), vegetable oils, non-toxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, benzyl alcohol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the substance in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Injectable solutions are particularly advantageous for local administration of the therapeutic composition. In particular, parenchymal injection can be used to deliver the therapeutic composition directly to a tumorous growth. Intra-articular injection is a preferred alternative in cases of arthritis where the practitioner wishes to treat one or only a few (such as 2-6) joints. Additionally, the therapeutic compounds are injected directly into lesions (intra-lesion administration) in appropriate cases. Intradermal administration is an alternative for dermal lesions.

The compounds of the present invention are optionally administered topically. Formulations suitable for topical administration include, for example, liniments, lotions, oil-in-water or water-in-oil emulsions such as creams, ointments or pastes, and solutions or suspensions. Ointments are semisolid preparations which are typically based on petrolatum or other petroleum derivatives. Creams containing the compound are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing. Formulations for topical administration may further comprise one or more of the additional ingredients described herein.

In one embodiment, the compound is delivered through the skin using transdermal drug delivery system. In a specific embodiment, the active ingredient is contained within a laminated structure that serves as a drug delivery device to be affixed to the skin— e.g. a patch. In such a structure, the drug composition is typically contained in a layer, or "reservoir," underlying an upper backing layer. The patch may contain a single reservoir, or it may contain multiple reservoirs.

In one particular embodiment of the present invention, the compounds and/or compositions described herein can be administered topically for the treatment of a abnormal cell proliferation disorder. In one embodiment, the disorder can be psoriasis. In another particular embodiment, the compounds and/or compositions described herein can be administered topically, for example, as a cream, for the treatment of psoriasis.

For pulmonary delivery, the compound may be administered to the lungs of a subject by any suitable means, but are preferably administered by administering an aerosol suspension of respirable particles comprised of the active compound, which the subject inhales. The respirable particles may be liquid or solid. The active compound can be aerosolized in a variety of forms, such as, but not limited to, dry powder inhalants, metered dose inhalants, or liquid/liquid suspensions.

In one embodiment, the formulation may contain the compound in the form of dry particles. Such compositions are conveniently in the form of dry powders for administration using a device comprising a dry powder reservoir to which a stream of propellant may be directed to disperse the powder or using a self-propelling solvent/powder-dispensihg container such as a device comprising the compound dissolved or suspended in a low-boiling propellant in a sealed container. Dry powder compositions preferably include a solid fine powder diluent such as sugar and are conveniently provided in a unit dose form.

In one embodiment, the formulation for pulmonary delivery provides the compound in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, for example, a flavoring agent such as saccharin sodium, a volatile oil, a buffering agent, a surface active agent, or a preservative such as methylhydroxybenzoate.

Aerosols of solid particles containing the active compound may be produced with any solid particulate medicament aerosol generator. Aerosol generators suitable for administering solid particulate medicaments to a subject produce particles which are respirable and generate a volume of aerosol containing a predetermined metered dose of a medicament at a rate suitable for human administration. A representative solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

The metered dose inhaler provides a second example of a solid particulate aerosol generator. Metered dose inhalers are pressurized aerosol dispensers, which typically contain a suspension or solution formulation of the active ingredient in a liquified propellant. During use these devices discharge the formulation through a valve adapted to deliver a metered volume, typically from 10 to 200 µL, to produce a fine particle spray containing the active ingredient. Suitable propellants include, for example, chlorofluorocarbon compounds (e.g., dichlorodifluoromethane, trichlorofluoromethane, dichlorotetrafluoroethane and mixtures thereof). The formulation may additionally contain one or more co-solvents, for example, ethanol, surfactants, such as oleic acid or sorbitan trioleate, antioxidants and suitable flavoring agents.

Aerosols of liquid particles comprising the active compound may be produced by any suitable means, such as with a pressure-driven jet aerosol nebulizer or an ultrasonic nebulizer. See, e.g., U.S. Pat. No. 4,501,729. Nebulizers transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w.

Solid or liquid particulate pharmaceutical formulations should include particles sizes should be within a range suitable for depositing a therapeutically effective amount in the lungs or in the airways, e.g., about 1-10 microns, to treat the lung condition of a patient in need of such treatment. Particles greater in size which are included in the aerosol tend to be deposited in the throat and swallowed, and the quantity of non-respirable particles in the aerosol is preferably minimized.

The formulations described herein as being useful for pulmonary delivery are also useful for intranasal delivery of a pharmaceutical composition of the invention. For nasal administration, a particle size in the range of 10-500 microns is preferred to ensure retention in the nasal cavity.

For ophthalmic applications, the therapeutic compound is formulated into solutions, suspensions, and ointments appropriate for use in the eye. For opthalmic formulations, see Mitra (ed.), Ophthalmic Drug Delivery Systems, Marcel Dekker, Inc., New York, N.Y. (1993), and also Havener, W. H., Ocular Pharmacology, C.V. Mosby Co., St. Louis (1983).

In one embodiment of the present invention, the compounds are prepared with carriers that will protect the compound against rapid elimination from the body, such as controlled release formulations. Controlled release formulations include, for example, delayed release or extended release formulations. The controlled-release of the compound can be controlled in any way suitable for achieving the desired result. Books describing methods of controlled delivery that are appropriate for the delivery of 4-PBA include: Robert S. Langer, Donald L. Wise, editors; *Medical applications of controlled release* (Volumes 1 and 2); Boca Raton, Fla.: CRC Press, 1984; and William J. M. Hrushesky, Robert Langer and Felix Theeuwes, editors; *Temporal control of drug delivery* (series); New York: New York Academy of Sciences, 1991. Representative, non-limiting systems suitable for use in the present invention include diffusion controlled, solvent controlled and chemically controlled systems.

Diffusion controlled systems suitable for use in the present invention include systems involving (i) diffusion through a membrane; and (ii) diffusion through a bulk polymer. In a membrane system, otherwise known as a reservoir device, diffusion of water through the polymer membrane is the rate determining step. Reservoir devices include oral, implantable or transdermal systems, for example. In one embodiment of the present invention, the active ingredient is encapsulated within a polymer film or coat. Representative, non-limiting polymers include cellulose ester, cellulose ether, an acrylic polymer, or a mixture of polymers.

In one embodiment of the present invention, sustained release of the compound is achieved through microencapsulation. Microcapsules are defined as microparticles having an outer polymer shell surrounding a core of another material, in this case, the compound of the present invention. The size of a microcapsule can vary from just a few microns to several millimeters. The microencapsulation drug delivery system may utilize any of a number of protective wall or covering materials, including proteins, polysaccharides, starches, waxes, fats, polymers and resins.

In one embodiment of the present invention, controlled release of the compound is achieved using a monolithic (matrix) device. Release is by continuous leaching of the drug from the polymer matrix core. Monolithic device may be formed, for example, by the compression of the polymer/drug mixture or by dissolution or melting. One type of matrix formulation is a matrix tablet, which is a matrix formulation in tablet form. The rate of release through the bulk polymer depends upon the amount of drug present at a particular time, and is therefore time dependent.

The three major types of materials suitable for use in the preparation of matrix devices include (i) insoluble plastics; (ii) hydrophilic polymers; and (iii) fatty compounds. Plastic matrixes are chemically inert and have a good drug embedding ability. Examples of suitable thermoplastic polymers are those having formulas incorporating monomeric units such as lactides, glycolides, caprolactones, anhydrides, amides, urethanes, esteramides, orthoesters, dioxanones, acetals, ketals, carbonates, phosphazenes, hydroxybutyrates, hydroxyvalerates, alkylene oxalates, alkylene succinates, and amino acids. Copolymers of any combination of lactide, caprolactone, and glycolide monomeric units are preferred.

Representative hydrophilic polymers suitable for use in a polymer matrix include cellulose derivatives, noncellulose polysaccharides, polyethylene oxide, polyvinyl alcohols and acrylic acid copolymers. Representative, non-limiting examples of cellulose derivatives include methylcellulose, hydroxypropyl methylcellulose (HPMC), hydroxyethyl cellulose, hydroxypropyl cellulose, carboxymethylcellulose, hydroxomethylcellulose, hemicellulose, and methylcellulose.

Fatty compounds include, but are not limited to, fatty excipients including glycerides (e.g., mono-, di- or triglycerides such as stearin, palnitin, laurin, myristin, hydrogenated castor or cottonseed oils, precirol), fatty acids and alcohols (e.g., stearic, palmitic or lauric acids; stearyl, cetyl or ceto-stearyl alcohols), fatty acid esters (e.g., monostearates of propylene glycol and of sucrose, sucrose distearate) and waxes (e.g., white wax, cachalot wax).

The matrix may include a single polymer type or multiple polymer types (i.e., a polymer blend). Representative U.S. patent disclosing polymer blends include U.S. Pat. No. 5,128, 143 (Baichwal et al.) entitled "Sustained Release Excipient and Tablet Formation"; U.S. Pat. No. 4,842,866 (Horder et al) entitled "Slow Release Solid Preparation"; U.S. Pat. No. 5,811,126 (Krishnamurthy) entitled "Controlled Release Matrix for Pharmaceuticals"; U.S. Pat. No. 3,965,256 (Leslie) entitled "Slow Release Pharmaceutical Composition"; and U.S. Pat. No. 4,235,870 (Leslie) entitled "Slow Release Pharmaceutical Compositions." In a polymer blend, the ratio of the two polymer types may be equal or different. A representative, non-limiting example of a hydrophilic polymer blend is a polyvinyl alcohol (PVA) and polyvinyl pyrrolidone (PVP)-based matrix.

The devices with different drug release mechanisms described above could be combined in a final dosage form comprising single or multiple units. Examples of multiple units include multilayer tablets, capsules containing tablets, beads, granules, etc.

Osmotically controlled systems are also suitable for use in the present invention. The osmotic pump is one such system. It is similar to a reservoir device but contains an osmotic agent (e.g., the active agent in salt form) which acts to imbibe water from the surrounding medium via a semi-permeable membrane. See Theeuwes F., Elementary Osmotic Pump., *J. Pharm. Sci.*, 64 (12), 1987-1991, 1975.

Chemically controlled systems are also suitable for use in the present invention. Chemically controlled systems include (i) erosion based systems; and (ii) pendant systems (i.e., combination of hydrolysis of pendant group and diffusion from bulk polymer). One type of erosion based system is a biodegradable polymer-based system. Representative, non-limiting examples of biodegradable polymers include naturally occurring biodegradable polymers such as alginate, dextrin, cellulose, collagen, chitosan; chemically or enzymatrically modified naturally occurring biodegradable polymers; and synthetic biodegradable polymers, such as polyanhydrides, polyesters, polyacrylic acids polyurethanes, polyphosphoesters and polyphosphazenes and poly(methyl methacrylates.

Non-limiting examples of U.S. Patents that describe controlled release formulations are: U.S. Pat. No. 5,356,630 to Laurencin et al. (Delivery System for Controlled Release of Bioactive Factors); U.S. Pat. No. 5,797,898 to Santini, Jr. et al. (Microchip Drug Delivery Devices); U.S. Pat. No. 5,874,064 to Edwards et al. (Aerodynamically Light Particles for Pulmonary Drug Delivery); U.S. Pat. No. 5,548,035 to Kim et al. (Biodegradable Copolymer as Drug Delivery Matrix Comprising Polyethyleneoxide and Aliphatic Polyester Blocks); U.S. Pat. No. 5,532,287 to Savage et al. (Radiation Cured Drug Release Controlling Membrane); U.S. Pat. No. 5,284,831 to Kahl et al. (Drug Delivery Porphyrin Composition and Methods); U.S. Pat. No. 5,741,329 to Agrawal et al. (Methods of Controlling the pH in the Vicinity of Biodegradable Implants); U.S. Pat. No. 5,820,883 to Tice et al. (Methods for Delivering Bioactive Agents into and Through the Mucosally-Associated Lymphoid Tissues and Controlling Their Release); U.S. Pat. No. 5,955,068 to Gouin et al. (Biodegradable polyanhydrides Derived from Dimers of Bile Acids and Use Thereof as Controlled Drug Release Systems); U.S. Pat. No. 6,001,395 to Coombes et al. (Polymeric Lamellar Substrate Particles for Drug Delivery); U.S. Pat. No. 6,013,853 to Athanasiou et al. (Continuous Release Polymeric Implant Carriers); U.S. Pat. No. 6,060,582 to Hubbell et al. (Photopolymerizable Biodegradable Hydrogels as Tissue Contacting Materials and Controlled Release Carriers); U.S. Pat. No. 6,113,943 to Okada et al. (Sustained-Release Preparation Capable of Releasing a Physiologically Active Substance); and PCT Publication No. WO 99/59548 to Oh et al. (Controlled Drug Delivery System Using the Conjugation of Drug to Biodegradable Polyester); U.S. Pat. No. 6,123,861 (Fabrication of Microchip Drug Delivery Devices); U.S. Pat. No. 6,060,082 (Polymerized Liposomes Targeted to M cells and Useful for Oral or Mucosal Drug Delivery); U.S. Pat. No. 6,041,253 (Effect of Electric Field and Ultrasound for Transdermal Drug Delivery); U.S. Pat. No. 6,018,678 (Transdermal protein delivery or measurement using low-frequency sonophoresis); U.S. Pat. No. 6,007,845 Nanoparticles And Microparticles Of Non-Linear Hydrophilic-Hydrophobic Multiblock Copolymers; U.S. Pat. No. 6,004,534 Targeted Polymerized Liposomes For Improved Drug Delivery; U.S. Pat. No. 6,002,961 Transdermal Protein Delivery Using Low-Frequency Sonophoresis; U.S. Pat. No. 5,985,309 Preparation Of Particles For Inhalation; U.S. Pat. No. 5,947,921 Chemical And Physical Enhancers And Ultrasound For Transdermal Drug Delivery; U.S. Pat. No. 5,912,017 Multiwall Polymeric Microspheres; U.S. Pat. No. 5,911,223 Introduction Of Modifying Agents Into Skin By Electroporation; U.S. Pat. No. 5,874,064 Aerodynamically Light Particles For Pulmonary Drug Delivery; U.S. Pat. No. 5,855,913 Particles Incorporating Surfactants For Pulmonary Drug Delivery; U.S. Pat. No. 5,846,565 Controlled Local Delivery Of Chemotherapeutic Agents For Treating Solid Tumors; U.S. Pat. No. 5,837,752 Semi-Interpenetrating Polymer Networks; U.S. Pat. No. 5,814,599 Transdermal Delivery Of Encapsulated Drugs; U.S. Pat. No. 5,804,178 Implantation Of Cell-Matrix Structure Adjacent Mesentery, Omentum Or Peritoneum Tissue; U.S. Pat. No. 5,797,898 Microchip Drug Delivery Devices; U.S. Pat. No. 5,770,417 Three-Dimensional Fibrous Scaffold Containing Attached Cells For Producing Vascularized Tissue In vivo; U.S. Pat. No. 5,770,193 Preparation Of Three-Dimensional Fibrous Scaffold For Attaching Cells To Produce Vascularized Tissue In vivo; U.S. Pat. No. 5,762,904 Oral Delivery Of Vaccines Using Polymerized Liposomes; U.S. Pat. No. 5,759,830 Three-Dimensional Fibrous Scaffold Containing Attached Cells For Producing Vascularized Tissue In vivo; U.S. Pat. No. 5,749,847 Delivery Of Nucleotides Into Organisms By Electroporation; U.S. Pat. No. 5,736,372 Biodegradable Synthetic Polymeric Fibrous Matrix Containing Chondrocyte For In vivo Production Of A Cartilaginous Structure; U.S. Pat. No. 5,718,921 Microspheres Comprising Polymer And Drug Dispersed There Within; U.S. Pat. No. 5,696,175 Preparation Of Bonded Fiber Structures For Cell Implantation; U.S. Pat. No. 5,667,491 Method For Rapid Temporal Control Of Molecular Transport Across Tissue; U.S. Pat. No. 5,654,381 Functionalized Polyester Graft Copolymers; U.S. Pat. No. 5,651,986 Controlled Local Delivery Of Chemotherapeutic Agents For Treating Solid Tumors; U.S. Pat. No. 5,629,009 Delivery System For Controlled Release Of Bioactive Factors; U.S. Pat. No. 5,626,862 Controlled Local Delivery Of Chemotherapeutic Agents For Treating Solid Tumors; U.S. Pat. No. 5,593,974 Localized Oligonucleotide Therapy; U.S. Pat. No. 5,578,325 Nanoparticles And Microparticles Of Non-Linear Hydrophilic-Hydrophobic Multiblock Copolymers; U.S. Pat. No. 5,562,099 Polymeric Microparticles Containing Agents For Imaging; U.S. Pat. No. 5,545,409 Delivery System For Controlled Release Of Bioactive Factors; U.S. Pat. No. 5,543,158 Biodegradable Injectable Nanoparticles; U.S. Pat. No. 5,514,378 Biocompatible Polymer Membranes And Methods Of Preparation Of Three Dimensional Membrane Structures; U.S. Pat. No. 5,512,600 Preparation Of Bonded Fiber Structures For Cell Implantation; U.S. Pat. No. 5,500,161 Method For Making Hydrophobic Polymeric Microparticles; U.S. Pat. No. 5,487,390 Gas-filled polymeric microbubbles for ultrasound imaging; U.S. Pat. No. 5,399,665 Biodegradable polymers for cell transplantation; U.S. Pat. No. 5,356,630 Delivery system for controlled release of bioactive factors; U.S. Pat. No. 5,330,768 Controlled drug delivery using polymer/pluronic blends; U.S. Pat. No. 5,286,763 Bioerodible polymers for drug delivery in bone; U.S. Pat. No. 5,149,543 Tonically cross-linked polymeric microcapsules; U.S. Pat. No. 5,128,420 Method of making hydroxamic acid polymers from primary amide polymers; U.S. Pat. No. 5,122,367 Polyanhydride bioerodible controlled release implants for administration of stabilized growth hormone; U.S. Pat. No. 5,100,668 Controlled release systems containing heparin and growth factors; U.S. Pat. No. 5,019,379 Unsaturated polyanhydrides; U.S. Pat. No. 5,010,167 Poly(amide- and imide-co-anhydride) for biological application; U.S. Pat. No. 4,948,587 Ultrasound enhancement of transbuccal drug delivery; U.S. Pat. No. 4,946,929 Bioerodible articles useful as implants and prostheses having predictable degradation rates; U.S. Pat. No. 4,933,431 One step preparation of poly(amide-anhydride); U.S. Pat. No. 4,933,185 System for controlled release of biologically active compounds; U.S. Pat. No. 4,921,757 System for delayed and pulsed release of biologically active substances; U.S. Pat. No. 4,916,204 Pure polyanhydride from dicarboxylic acid and coupling agent; U.S. Pat. No. 4,906,474 Bioerodible polyanhydrides for controlled drug delivery; U.S. Pat. No. 4,900,556 System for delayed and pulsed release of biologically active substances; U.S. Pat. No. 4,898,734 Polymer composite for controlled release or membrane formation; U.S. Pat. No. 4,891,225 Bioerodible polyanhydrides for controlled drug delivery; U.S. Pat. No. 4,888,176 Controlled drug delivery high molecular weight polyanhydrides; U.S. Pat. No. 4,886,870 Bioerodible articles useful as implants and prostheses having predictable degradation rates; U.S. Pat. No. 4,863,735 Biodegradable polymeric drug delivery system with adjuvant activity; U.S. Pat. No. 4,863,611 Extracorporeal reactors containing immobilized species; U.S. Pat. No. 4,861,627 Preparation of multiwall polymeric microcapsules; U.S. Pat. No. 4,8,57,311 Polyanhydrides with improved hydrolytic degradation properties; U.S. Pat. No. 4,846,786 Bioreactor containing suspended, immobilized species; U.S. Pat. No. 4,806,621 Biocompatible, bioerodible, hydrophobic, implantable polyimino carbonate article; U.S. Pat. No. 4,789,724 Preparation of anhydride copolymers; U.S. Pat. No. 4,780,212 Ultrasound enhancement of membrane permeability; U.S. Pat. No. 4,779,806 Ultrasonically modulated polymeric devices for delivering compositions; U.S. Pat. No. 4,767,402 Ultrasound enhancement of transdermal drug delivery; U.S. Pat. No. 4,757,128 High molecular weight polyanhydride and preparation thereof; U.S. Pat. No. 4,657,543 Ultrasonically modulated polymeric devices for delivering compositions; U.S. Pat. No. 4,638,045 Non-peptide polyamino acid bioerodible polymers; U.S. Pat. No. 4,591,496 Process for making systems for the controlled release of macromolecules.

Drug Delivery on a Stent, Balloon or other Device

The compounds and compositions of the present invention can be delivered via a medical device. Any insertable or implantable medical device, including, but not limited to stents, catheters, balloon catheters, shunts or coils. In one embodiment, the present invention provides medical devices, such as stents, the surface of which is coated with a compound or composition as described herein. The medical device of this invention can be used, for example, in any application for treating, preventing, or otherwise affecting the course of a disease or tissue or organ dysfunction, such as the diseases disclosed herein. A stent can beany tubular structure used to maintain or support a bodily orifice or cavity. Stent can be a scaffolding, usually cylindrical in shape, that can be inserted into a body passageway or a portion of a body passageway, which has been narrowed, irregularly contured, obstructed, or occluded by a disease process in order to prevent closure or reclosure of the passageway. Stents act by physically holding open the walls of the body passage into which they are inserted. A balloon catheter can be a tubular instrument with a balloon or multiple balloons that can be inflated or deflated without removal after insertion into the body.

Additional examples of implantable medical devices include, but are not limited to, stents, stent grafts, stent covers, catheters, artificial heart valves and heart valve scaffolds, venous access devices, vena cava filters, peritoneal access devices, and enteral feeding devices used in percutaneous endoscopic gastronomy, prosthetic joints and artificial ligaments and tendons. Stents include, but are not limited to esophageal stents, vascular stents, biliary stents, pancreatic stents, ureteric and urethral stents, lacrimal stents, Eustachian tube stents, fallopian tube stents and tracheal/bronchial stents. Stents can be coiled or patterned as a braided or woven open network of fibers or filaments or, for example, as an interconnecting open network of articulable segments. Such stent designs can be useful for maintaining the patency of a body lumen such as a coronary artery. Stents adapted primarily to provide drainage, in contrast to stents adapted primarily to support a body lumen, can have a continuous wall structure in contrast to an open network wall structure.

Stents can be readily obtained from commercial sources, or constructed in accordance with well-known techniques. Representative examples of stents include those described in U.S. Pat. No. 4,768,523, entitled "Hydrogel Adhesive;" U.S. Pat. No. 4,776,337, entitled "Expandable Intraluminal Graft, and Method and Apparatus for Implanting and Expandable Intraluminal Graft;" U.S. Pat. No. 5,041,126 entitled "Endovascular Stent and Delivery System;" U.S. Pat. No. 5,052,998 entitled "Indwelling Stent and Method of Use;" U.S. Pat. No. 5,064,435 entitled "Self-Expanding Prosthesis Having Stable Axial Length;" U.S. Pat. No. 5,089,606, entitled "Water-insoluble Polysaccharide Hydrogel Foam for Medical Applications;" U.S. Pat. No. 5,147,370, entitled "Nitinol Stent for Hollow Body Conduits;" U.S. Pat. No. 5,176,626, entitled "Indwelling Stent;" U.S. Pat. No. 5,213,580, entitled "Biodegradable polymeric Endoluminal Sealing Process;" and U.S. Pat. No. 5,328,471, entitled "Method and Apparatus for Treatment of Focal Disease in Hollow Tubular Organs and Other Tissue Lumens."

Stents can be coated with the compounds and compositions of the present invention in a variety of manners known to one skilled in the art, including, but not limited to: (a) by directly affixing to the stent an compound or composition described herein (e.g., by either spraying the stent with a polymer/drug film, or by dipping the stent into a polymer/drug solution), (b) by coating the stent with a substance such as a hydrogel which will in turn absorb the compounds or compositions, (c) by interweaving compounds or composition coated thread (or the polymer itself formed into a thread) into the stent structure, (d) by inserting the stent into a sleeve or mesh which is comprised of or coated with a compounds or composition of the present invention, or (e) constructing the stent itself with a compounds or composition described herein. Therefore, in one embodiment of the present invention, the compounds are applied, attached, dripped and/or embedded to the stent by known methods. Within particular embodiments of the invention, the composition should firmly adhere to the stent during storage and at the time of insertion, and should not be dislodged from the stent when the diameter is expanded from its collapsed size to its full expansion size. The composition should also preferably not degrade during storage, prior to insertion, or when warmed to body temperature after expansion inside the body. In addition, it can coat the stent smoothly and evenly, with a uniform distribution of the compound, while not changing the stent contour.

In one embodiment, the stent structure can include a plurality of holes or, in a separate embodiment, a plurality of recesses which can act as reservoirs and can be loaded with the drug. The stent can be designed with particular sites that can incorporate the drug, or multiple drugs, optionally with a biodegradable or non-biodegradable matrix. The sites can be holes, such as laser drilled holes, or recesses in the stent structure that can be filled with the drug or can be partially filled with the drug. In one embodiment, a portion of the holes are filled with other therapeutic agents, or with materials that regulate the release of the drug or drugs. One advantage of this system is that the properties of the coating can be optimized for biocompatibility and adhesion properties, without the addition requirement of being able to load and release the drug. The size, shape, position, and number of reservoirs can be used to control the amount of drug, and therefore the dose delivered.

Within another aspect of the present invention, methods are provided for expanding the lumen of a body passageway, comprising inserting a stent into the passageway, the stent having a generally tubular structure, the surface of the structure being coated with a compound or composition of the present invention, such that the passageway is expanded.

Generally, stents can be inserted in a similar fashion regardless of the site or the disease being treated, such as via techniques known to one skilled in the art. Briefly, a preinsertion examination, usually a diagnostic imaging procedure, endoscopy, or direct visualization at the time of surgery, is generally first performed in order to determine the appropriate positioning for stent insertion. A guidewire is then advanced through the lesion or proposed site of insertion, and over this is passed a delivery catheter which allows a stent in its collapsed form to be inserted. Typically, stents are capable of being compressed, so that they can be inserted through tiny cavities via small catheters, and then expanded to a larger diameter once they are at the desired location. Once expanded, the stent physically forces the walls of the passageway apart and holds them open. As such, they are capable of insertion via a small opening, and yet are still able to hold open a large diameter cavity or passageway. The stent can be self-expanding (e.g., the Wallstent and Gianturco stents), balloon expandable (e.g., the Palmaz stent and Strecker stent), or implanted by a change in temperature (e.g., the Nitinol stent).

Stents can be maneuvered into place under radiologic or direct visual control, taking particular care to place the stent precisely across the narrowing in the organ being treated. The delivery catheter is then removed, leaving the stent standing on its own as a scaffold. A post insertion examination, usually an x-ray, is often utilized to confirm appropriate positioning.

VI. Therapeutic Uses

The formulations comprising the compound of the present invention can be used for a number of therapeutic applications. Notably, the compounds can be used to treat disorders characterized by abnormal cell proliferation, inflammation, or both abnormal proliferation and inflammation.

A. Disorders of Abnormal Cell Proliferation

The compositions of the present invention are useful in the treatment or prevention of abnormal cell proliferation. As used herein, a "abnormal cell proliferation disorder" refers to a disease or disorder characterized by the inappropriate growth or multiplication of one or more cell types relative to the growth of that cell type or types in an individual not suffering from that disease or disorder. Abnormal cell proliferation has been shown to be the root of many diseases and disorders, including cancer and non-cancer disorders which present a serious health threat.

The term "treatment" refers to methods of killing, inhibiting or slowing the growth or increase in size of a body or population of abnormally proliferative cells or tumor or cancerous growth, reducing the number of cells in the population of abnormally proliferative cells, or preventing the spread of abnormally proliferative cells to other anatomic sites, as well as reducing the size of a growth of abnormally proliferative cells. The term "treatment" does not necessarily mean to imply a cure or a complete abolition of the disorder of abnormal cell proliferation. The term "prevention" refers to methods to which slow, delay, control or decrease the likelihood of the incidence or onset of disorders of abnormal cell proliferation, in comparison to that which would occur in the absence of treatment.

Abnormal cellular proliferation, notably hyperproliferation, can occur as a result of a wide variety of factors, including genetic mutation, infection, exposure to toxins, autoimmune disorders, and benign or malignant tumor induction. Hyperproliferative cell disorders include, but are not limited to, skin disorders, blood vessel disorders, cardiovascular disorders, fibrotic disorders, mesangial disorders, autoimmune disorders, graft-versus-host rejection, tumors and cancers.

Non-neoplastic Abnornal Cellular Proliferation Disorders

Skin disorders associated with cellular hyperproliferation, including, but are not limited to, psoriasis (all types), eczerma, acne vulgaris, acne, rosacea, common warts, anogenital (venereal) warts, eczema; lupus associated skin lesions; dermatitides such as atopic dermatitis, seborrheic dermatitis and solar dermatitis; keratoses such as seborrheic keratosis, senile keratosis, actinic keratosis, photo-induced keratosis, skin ageing, including photo-induced skin aging, keratosis follicularis; keloids, eukoplakia, lichen planus, keratitis, contact dermatitis, urticaria, pruritus, hidradenitis, and acne inverse; pemphigus vulgaris, actinic keratosis, basal cell carcinoma and squamous cell carcinoma.

In a particular embodiment, the compounds of the present invention are useful in the treatment of psoriasis. Psoriasis is an immune-mediated skin disorder characterized by chronic T-cell stimulation by antigen-presenting cells (APC) occurs in the skin. Approximately 2-3% of the global population is afflicted by psoriasis. While the cause of psoriasis remains poorly understood, it appears to result from a combination of genetic and environmental factors. The various types of psoriasis include, for example, plaque psoriasis (i.e., vulgaris psoriasis), pustular psoriasis, guttate psoriasis, inverse psoriasis, erythrodermic psoriasis, psoriatic arthritis, scalp psoriasis and nail psoriasis. Psoriasis is a lifelong disease characterized by spontaneous remissions and exacerbations. Common systemic treatments for psoriasis include methotrexate, cyclosporin and oral retinoids, but their use is limited by toxicity. Up to 40% of patients with psoriasis also develop psoriatic arthritis (Kormeili T et al. *Br J Dermatol.* (2004) 151(1):3-15.

Blood vessel proliferative disorders include vasculogenic (formation) and angiogenic (spreading) disorders which result in abnormal proliferation of blood vessels. Other blood vessel proliferative disorders include arthritis and ocular diseases such as diabetic retinopathy. Abnormal neovascularization is also associated with solid tumors. In a particular embodiment, the compounds of the present invention are useful in the treatment of diseases associated with uncontrolled angiogenesis Representative, non-limiting diseases of abnormal angiogenesis include, e.g., rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome. Cancers associated with abnormal blood cell proliferation include hemangioendotheliomas, hemangiomas and Kaposi's sarcoma.

Disorders of the cardiovascular system involving abnormal cell proliferation include, for example, hypertension, vasculo-occlusive diseases (e.g., atherosclerosis, thrombosis and restenosis after angioplasty), acute coronary syndromes such as unstable angina, myocardial infarction, ischemic and non-ischemic cardiomyopathies, post-MI cardiomyopathy and myocardial fibrosis, substance-induced cardiomyopathy.

Atherosclerosis represents one type of abnormal smooth muscle cell proliferation. As used herein, atheroscloeris refers to classical atherosclerosis, accelerated atherosclerosis, atherosclerotic lesions and any other arteriosclerotic conditions characterized by undesirable endothelial and/or vascular smooth muscle cell proliferation, including vascular complications of diabetes. Classical atheroscloeris is characterized by proliferation of vascular smooth muscle cells. Growth factors released from endothelial cells are thought to stimulate the proliferation of subintimal smooth muscle which, in turn, reduces the caliber and finally obstructs the artery. The invention is useful in inhibiting such proliferation, and therefore in delaying the onset of, inhibiting the progression of, or even stopping the progression of such proliferation. Accelerated atherosclerosis is responsible for the failure of many heart transplants that are not rejected. Here, proliferation is also mediated by growth factors, and can produce obstruction of the coronary arteries.

Vascular injury can also result in endothelial and vascular smooth muscle cell proliferation. The injury can be caused by traumatic events or interventions (e.g., angioplasty, vascular graft, anastomosis, organ transplant) (Clowes A et al. *A. J. Vasc. Surg* (1991) 13:885). Restenosis (e.g. coronary, carotid, and cerebral lesions) is the main complication of successful balloon angioplasty of the coronary arteries. It is believed to be caused by the release of growth factors as a result of mechanical injury to the endothelial cells lining the coronary arteries.

Other atherosclerotic conditions which can be treated or prevented by means of the present invention include diseases of the arterial walls that involve proliferation of endothelial and/or vascular smooth muscle cells, including complications of diabetes, diabetic glomerulosclerosis and diabetic retinopathy.

Abnormal cell proliferation disorders associated the endrocine system include, for example, insulin resistant states including obesity, diabetes mellitus (types 1 & 2), diabetic retinopathy, macular degeneration associated with diabetes, gestational diabetes, impaired glucose tolerance, polycystic ovarian syndrome; osteoporosis, osteopenia, accelerated aging of tissues and organs including Werner's syndrome.

The compositions and methods of the present invention are also useful for treating inflammatory diseases associated with abnormal cell proliferation. These include, but are not limited, to inflammatory bowel disease (IBD), rheumatoid arthritis (RA), multiple sclerosis (MS), proliferative glomerulonephritis, lupus erythematosus, scleroderma, temporal arteritis, thromboangiitis obliterans, mucocutaneous lymph node syndrome, asthma, host versus graft, thyroiditis, Grave's disease, antigen-induced airway hyperactivity, pulmonary eosinophilia, Guillain-Barre syndrome, allergic rhinitis, myasthenia gravis, human T-lymphotrophic virus type 1-associated myelopathy, herpes simplex encephalitis, inflammatory myopathies; atherosclerosis, and Goodpasture's syndrome. These diseases are considered in more detail below, under "Disorders of Inflammation."

Abnormal cell proliferation disorders of the urogenital system can also be treated according to the present invention. These include, for example, edometriosis, benign prostatic hyperplasia, eiomyoma, polycystic kidney disease, and diabetic nephropathy.

Treatment of fibrotic disorders is contemplated in the present invention. As used herein, fibrotic disorders refers to fibrosis and other medical complications of fibrosis which result in whole or in part from the proliferation of fibroblasts. Medical conditions involving fibrosis include undesirable tissue adhesion resulting from surgery or injury. Non-limiting examples of fibrotic disorders include hepatic cirrhosis and mesangial proliferative cell disorders.

Abnormal cell proliferation disorders of the tissues and joints can be treated according to the present invention including, for example, Raynaud's phenomenon/disease, Sjogren's Syndrome systemic sclerosis, systemic lupus erythematosus, vasculitides, ankylosing spondylitis, osteoarthritis, reactive arthritis, psoriatic arthritis, fibrormyalgia.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Abnormal cell proliferation disorders of the pulmonary system can also be treated according to the present invention including, for example, asthma, chronic obstructive pulmonary disease (COPD), reactive airway disease, pulmonary fibrosis, pulmonary hypertension.

Other disorders that can include an abnormal cellular proliferative component include Behcet's syndrome, Fibrocystic breast disease, fibroadenoma, chronic fatigue syndrome, acute respiratory distress syndrome (ARDS), ischemic heart disease, post-dialysis syndrome, leukemia, acquired immune deficiency syndrome, vasculitis, lipid histiocytosis, septic shock, familial intestinal polyposes such as Gardner syndrome.

Also included in the scope of disorders that may be treated by the compositions and methods of the present invention are virus-induced hyperproliferative diseases including, for example, human papilloma virus-induced disease (e.g., lesions caused by human papilloma virus infection), Epstein-Barr virus-induced disease, scar formation, genital warts, cutaneous warts, and the like.

Neoplastic Abnormal Cellular Proliferation Disorders

Diseases of abnormal cell proliferation include various types of cancers such as primary tumors and tumor metastasis. The term "cancer" includes both tumor-forming or non-tumor forming cancers. As used herein, the term "tumor" means an abnormal mass of cells within a multicellular organism. Generally, the growth of the abnormal cells of the tumor exceeds and is uncoordinated with that of normal cells. Furthermore, the abnormal growth of tumor cells generally persists in an abnormal (i.e., excessive) manner after the cessation of stimuli that originally caused the abnormality in the growth of the cells. Tumors can be malignant or benign. A benign tumor is characterized by cells that retain their differentiated features and do not divide in a completely uncontrolled manner. A benign tumor is usually localized and non-metastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

A malignant tumor (i.e., cancer) is characterized by cells that are undifferentiated, do not respond to the body's growth control signals, and multiply in an uncontrolled manner one. Maligant tumors are invasive and capable of metastasis. Representative, non-limiting cancers include breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The compounds of the present invention are also useful in preventing or treating proliferative responses associated with organ transplantation which contribute to rejections or other complications. For example, proliferative responses may occur during transplantation of the heart, lung, liver, kidney, and other body organs or organ systems.

B. Inflammation Disorders

The compounds of the present invention are also useful in the treatment of diseases characterized by inflammation. Diseases and disorders which have significant inflammatory components are ubiquitous and include, for example, skin disorders, bowel disorders, certain degenerative neurological disorders, arthritis, autoimmune diseases and a variety of other illnesses. Some of these diseases have both an inflammatory and proliferative component, as described above under "Abnormal Cell Proliferation."

(i) Inflammatory Bowel Disease

Inflammatory bowel diseases (IBD) includes several chronic inflammatory conditions, including Crohn's disease (CD) and ulcerative colitis (UC). Collectively, these diseases afflict between one and two million Americans and produce symptoms that impair quality of life and ability to function. Both CD and UC are considered "idiopathic" because their etiology is unknown. While the Crohn's disease and ulcerative colitis share many symptoms (e.g., diarrhea, abdominal pain, fever, fatigue), ulcerative colitis is limited to the colon whereas Crohn's disease can involve any segment of the gastrointestinal tract. Both diseases may involve extraintestinal manifestations, including arthritis, diseases of the eye (e.g., episcleritis and iritis), skin diseases (e.g., erythema nodosum and pyoderma gangrenosum), urinary complications, gallstones and anemia. Strokes, retinal thrombi, and pulmonary emboli are not uncommon, because many patients are in a hypercoagulable state.

While the etiology of IBD is unclear, a combination of environmental, infectious, genetic, autoimmune, and host factors have been suspected. Interactions among these factors may be more important. From a genetic standpoint, IBD is thought to involve genetically determined, deregulated immune responses to otherwise innocuous luminal antigens (Rev Lim W C. *Gastroenterol Disord*. (2004) 4(2):66-85). Bacterial organisms that can produce IBD include, for example, Shigella, Salmonella,. Campylobacter, H. pylori, and some *E. coli*. Bacteria are a common cause of acute self-limited colitis-active IBD without chronic changes. Recently, a clear association between complicated courses of ulcerative colitis and the presence of cytomegalovirus (CMV) has been established (Hommes D W. *Inflamm Bowel Dis*. (2004) 10(3):245-50).

In a particular embodiment, the compounds of the present invention, including pharmaceutically acceptable salts, prodrugs and esters thereof, are useful in the treatment of inflammatory bowel disease. In a preferred embodiment, the inflammatory bowel disease is Crohn's disease.

(ii) Chronic Obstructive Pulmonary Disease

Chronic Obstructive Pulmonary Disease, or COPD, is characterized by a not fully reversible airflow limitation which is progressive and associated with an abnormal inflammatory reaction of the lungs. It is one of the commonest respiratory conditions of adults, a major cause of chronic morbidity and mortality, and represents a substantial economic and social burden worldwide (Pauwels R A. *Lancet*. (2004) 364(9434):613-20). In the United States, COPD is currently the fourth leading cause of death (Molfino N A. *Chest*. (2004) 125(5):1929-40). The major risk factors for the development of COPD are inhaled toxic substances, such as smoke. Other names for the disorder include, for example, Chronic Obstructive Airways Disease, (COAD); Chronic Obstructive Lung Disease, (COLD), Chronic Airflow Limitation, (CAL or CAFL) and Chronic Airflow Obstruction (COA).

Chronic obstructive pulmonary disease (COPD) COPD is characterized by chronic inflammation throughout the airways, parenchyma, and pulmonary vasculature. The inflammation involves a multitude of cells, mediators, and inflammatory effects. Mediators include, for example, mediators include proteases, oxidants and toxic peptides. Over time, inflammation damages the lungs and leads to the pathologic changes characteristic of COPD. Manifestations of disease includes both chronic bronchitis and emphysema. Chronic bronchitis is a long-standing inflammation of the airways that produces a lot of mucus, causing wheezing and infections. It is considered chronic if a subject has coughing and mucus on a regular basis for at least three months a year and for two years in a row. Emphysema is a disease that destroys the alveolae and/or bronchae, causing the air sacs to become enlarged, thus making breathing difficult. Most common in COPD patients is the centrilobular form of emphysema.

In a particular embodiment, the compounds of the present invention are useful in the treatment of chronic obstructure pulmonary disease.

(iii) Sarcoidois

Sarcoidois is yet another chronic inflammatory disease with associated abnormal cell proliferation. Sarcoidois is a multisystem granulomatous disorder. The granulomas are created by the angiogenic capillary sprouts providing a constant supply of inflammatory cells. Psoriasis, also a chronic and recurrent inflammatory disease, is characterized by papules and plaques of various sizes. Treatment with the compounds of the present invention would prevent the formation of new blood vessels necessary to maintain the characteristic lesions.

(iv) Asthma

In recent years, it has become clear that the primary underlying pathology of asthma is airway tissue inflammation (Lemanke R F. *Pediatrics*. (2002)109(2):368-372; Nagayama Y et al. Pediatr Allergy Immunol. (1995) 6:204-208). Asthma is associated with a wide range of symptoms and signs, including wheezing, cough, chest tightness, shortness of breath and sputum production. Airway inflammation a key feature of asthma pathogenesis and its clinical manifestations. Inflammatory cells, including mast cells, eosinophils, and lymphocytes, are present even in the airways of young patients with mild asthma. Inflammation also plays a role in wheezing disorders, with or without asthma.

(v) Arthritis and Osteoarthritis

Arthritis means joint inflammation. More than 40 million Americans suffer from arthritis in its various forms, including includes over 100 kinds of rheumatic diseases (i.e., diseases affecting joints, muscle, and connective tissue, which makes up or supports various structures of the body, including tendons, cartilage, blood vessels, and internal organs). Representative types of arthritis include rheumatoid (such as soft-tissue rheumatism and non-articular rheumatism), fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus.

Hypertrophic arthritis or osteoarthritis is the most common form of arthritis. It is characterized by the breakdown of the joint's cartilage. Osteoarthritis is common in people over 65, but may appear decades earlier. Breakdown of the cartilage causes bones to rub against each other, causing pain and loss of movement. In recent years, there has been increasing evidence that inflammation plays an important role in osteoarthritis. Nearly one-third of patients ready to undergo joint replacement surgery for osteoarthritis (OA) had severe inflammation in the synovial fluid that surrounds and protects the joints.

In a particular embodiment, the compounds of the present invention are useful in the treatment of osteoarthritis.

The second most common form of arthritis is rheumatoid arthritis. It is an autoimmune disease that can affect the whole body, causing weakness, fatigue, loss of appetite, and muscle pain. Typically, the age of onset is much earlier than osteoarthritis, between ages 20 and 50. Inflammation begins in the synovial lining and can spread to the entire joint.

Other forms of arthritis include, for example, gout, ankylosing spondylitis, juvenile arthritis, psoriatic arthritis, systemic lupus erythematosus, infectious arthritis, scleroderma, and fibromyalgia syndrome. Asthma is sometimes classified by the triggers that may cause an asthma episode (or asthma attack) or the things that make asthma worse in certain individuals, such as occupational asthma, exercise induced asthma, nocturnal asthma, or steroid resistant asthma.

(vii) Cardiovascular Disease

As noted above, inflammation also plays an important role in the pathogenesis of cardiovascular diseases, including restenosis, atherosclerotic complications resulting from plaque rupture, severe tissue ischemia, and heart failure. Inflammatory changes in the arterial wall, for example, are thought to play a major role in the development of restenosis and atherosclerosis (Ross R. *N Engl J Med.* (1999) 340: 115-126). Local inflammation occurs in the formation the plaques also contributes to the weakening of the fibrous cap of the advanced plaque, ultimately resulting in plaque rupture and acute coronary syndromes (Lind L. Atherosclerosis. (2003) 169(2):203-14. Evidence suggests that mediators such as adhesion molecules, chemokines and cytokines are involved in the initiation and progression of atherosclerotic lesions. Dynamic instability of a coronary atherosclerotic plaque is understood as the foundation for the development of unstable angina and myocardial infarction (Smith D. *Circulation.* (2001) 104(7):746-9.

(ix) Multiple Sclerosis

Multiple sclerosis (MS) is a chronic, often debilitating autoimmune disease that affects the central nervous system. MS is characterized by inflammation which results when the The body directs antibodies and white blood cells against proteins in the myelin sheath, fatty material which insulates the nerves in the brain and spinal cord. The result may be multiple areas of scarring (sclerosis), which slows or blocks muscle coordination, visual sensation and other nerve signals. The severity of the disease may vary. Most MS patients have a relapsing form of the disease, involving exacerbations in which symptoms appear suddenly (i.e., within 24 hours). Various "triggers" of exacerbation have been proposed, including bacterial or viral infections that cause T cells to mistake myelin proteins for these antigens, bacterial superantigens, physical injury, or stressful life events (Hohlfeld R. *Neurology* (1995) 45(6 suppl 6): S33-8).

In a particular embodiment, the compounds of the present invention are useful in the treatment of multiple sclerosis.

(x) Neurological Disease

Inflammatory have been shown to be associated with the pathogenesis of neurological disorders, including Parkinson's disease and Alzheimer's disease (Mirza B. et al. *Neuroscience* (2000) 95(2):425-32; Gupta A. *Int J Clin Pract.* (2003) 57(1):36-9; Ghatan E. et al. *Neurosci Biobehav Rev.* (1999) 23(5):615-33).

(ix) Other Inflammatory Diseases

The present invention is also useful in the treatment of, for example, allergic disorders, allergic rhinitis, skin disorders, transplant rejection, poststreptococcal and autoimmune renal failure, septic shock, systemic inflammatory response syndrome (SIRS), adult respiratory distress syndrome (ARDS), envenomation, lupus erythmatosus, myasthenia gravis, Grave's disease, Hashimoto's thyroiditis, autoimmune hemolytic anemias, insulin dependent diabetes mellitus, glomerulonephritis, and rheumatic fever, pelvic inflammatory disease (PID), conjunctivitis, dermatitis, bronchitis, and rhinitis.

VII. Combination Therapies

Any of the compounds disclosed herein can be administered in combination or alternation with a second, and perhaps third, biologically active agent to increase its effectiveness against the target disorder. In combination therapy, effective dosages of two or more agents are administered together. In alternation therapy, an effective dosage of each agent is administered serially.

In general, combination therapy is typically preferred over alternation therapy because it induces multiple simultaneous stresses on the condition. Any method of alternation can be used that provides treatment to the patient. Nonlimiting examples of alternation patterns include 1-6 weeks of administration of an effective amount of one agent followed by 1-6 weeks of administration of an effective amount of a second agent. The alternation schedule can include periods of no treatment. Combination therapy generally includes the simultaneous administration of an effective ratio of dosages of two or more active agents.

Illustrative examples of specific agents that can be used in combination or alternation with the compounds of the present invention are described below. These agents can alternatively be in combination with the compounds of the present invention to treat a host suffering from any of the other disorders listed in Section F above.

A. Abnormal Cell Proliferation

The compounds of the present invention can be used in combination or alternation with antiproliferative agents. As used herein, an antiproliferative agent is a compound that decreases the hyperproliferation of cells. Proliferative disorders are currently treated by a variety of classes of compounds including alkylating agents, antimetabolites, natural products, enzymes, biological response modifiers, miscellaneous agents, radiopharmaceuticals (for example, Y-90 tagged to hormones or antibodies), hormones and antagonists. Any of the antiproliferative agents listed below or any other such therapeutic agents and principles as described in, for example, DeVita, V. T., Jr., Hellmann, S., Rosenberg, S. A.; In: Cancer: Principles & Practice of Oncology, 5th ed., Lippincott-Raven Publishers (1997) can be used in combination with the compounds of the present invention.

(i) Anti-angiogenesis Agents

Representative, nonlimiting examples of anti-angiogenesis agents suitable for use in combination with the compounds of the present invention include, but are not limited to, retinoid acid and derivatives thereof, 2-methoxyestradiol, Angiostatin™ protein, Endostatin™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((I-azetidine-2-carboxylic acid (LACA), cishydroxyproline, d,1-3, 4-dehydroproline, thiaproline], $\alpha,\alpha$-dipyridyl, $\beta$-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, $\beta$-cyclodextrin tetradecasulfate, eponemycin; fumagillin, gold sodium thiomalate, d-penicillamine (CDPT), $\beta$-1-anticollagenase-serum, $\alpha$-2-antiplasmin, bisantrene, lobenzarit disodium, n-(2-carboxyphenyl-4-chloroanthronilic acid disodium or "CCA", thalidomide; angostatic steroid, cargboxynaminolmidazole; metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

(ii) Alkylating Agents

Representative, nonlimiting examples of alkylating agents suitable for use in combination with the compounds of the present invention include, but are not limited to, Nitrogen Mustards, such as Mechlorethamine (Hodgkin's disease, non-Hodgkin's lymphomas), Cyclophosphamide, Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphoctic leukemia, primary macroglobulinemia, Hodgkin's disease, non-Hodgkin's lymphomas); Ethylenimines and Methylmelamines, such as, Hexamethylmelamine (ovary), Thiotepa (bladder, breast, ovary); Alkyl Sulfonates, such as, Busulfan (chronic granuloytic leukemia); Nitrosoureas, such as, Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (STR) (malignant pancreatic insulinoma, malignant carcinoin); Triazenes, such as, Dacarbazine (DTIC; dimethyltriazenoimidazole-carboxamide) (malignant melanoma, Hodgkin's disease, soft-tissue sarcomas).

(iii) Antimetabolites

Representative, nonlimiting examples of anti-metabolite agents suitable for use in combination with the compounds of the present invention include, but are not limited to, Folic Acid Analogs, such as, Methotrexate (amethopterin) (acute lymphocytic leukemia, choriocarcinoma, mycosis fungoides, breast, head and neck, lung, osteogenic sarcoma); Pyrimidine Analogs: Fluorouracil (5-fluorouracil; 5-FU) Floxuridine (fluorodeoxyuridine; FUdR) (breast, colon, stomach, pancreas, ovary, head and neck, urinary bladder, premalignant skin lesions) (topical), Cytarabine (cytosine arabinoside) (acute granulocytic and acute lymphocytic leukemias); Purine Analogs and Related Inhibitors, such as, Mercaptopurine (6-mercaptopurine; 6-MP) (acute lymphocytic, acute granulocytic and chronic granulocytic leukemia), Thioguanine (6-thioguanine: TG) (acute granulocytic, acute lymphocytic and chronic granulocytic leukemia), Pentostatin (2'-deoxycyoformycin) (hairy cell leukemia, mycosis fungoides, chronic lymphocytic leukemia); Vinca Alkaloids, such as, Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung); Epipodophylotoxins, such as Etoposide (testis, small-cell lung and other lung, breast, Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

(iv) Cytotoxic Agents

Representative cytotoxic agents include, but are not limited to: doxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci. *Physicians' Desk Reference,* 50th Edition, 1996.

(v) Natural Products

Representative natural products include, but are not limited to: Antibiotics, such as, Dactinomycin (actinonmycin D) (choriocarcinoma, Wilms' tumor rhabdomyosarcoma, testis, Kaposi's sarcoma), Daunorubicin (daunomycin; rubidomycin) (acute granulocytic and acute lymphocytic leukemias), Doxorubicin (soft tissue, osteogenic, and other sarcomas; Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcema), Mitomycin (mitomycin C) (stomach, cervix, colon, breast, pancreas, bladder, head and neck); Enzymes, such as, L-Asparaginase (acute lymphocytic leukemia); Biological Response Modifiers, such as, Interferon-alfa (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

(vi) Miscellaneous Agents

Additional agents that can be used in combination or alternation with the compounds and compositions disclosed herein include, but are not limited to: Platinum Coordination Complexes, such as, Cisplatin (cis-DDP) Carboplatin (testis, ovary, bladder, head and neck, lung, thyroid, cervix, endometrium, neuroblastoma, osteogenic sarcoma); Anthracenedione, such as Mixtozantrone (acute granulocytic leukemia, breast); Substituted Urea, such as, Hydroxyurea (chronic granulocytic leukemia, polycythemia vera, essential thrombocytosis, malignant melanoma); Methylhydrazine Derivatives, such as, Procarbazine (N-methylhydrazine, MIH) (Hodgkin's disease); Adrenocortical Suppressants, such as, Mitotane (o,p'-DDD) (adrenal cortex), Aminoglutethimide (breast); Adrenorticosteriods, such as, Prednisone (acute and chronic lymphocytic leukemias, non-Hodgkin's lymphomas, Hodgkin's disease, breast); Progestins, such as, Hydroxprogesterone caproate, Medroxyprogesterone acetate, Megestrol acetate (endometrium, breast); Steroids, such as, include betamethasone sodium phosphate and betamethasone acetate.

(vii) Hornones and Antagonists

Representative, nonlimiting examples of hormones and antagonists suitable for use in combination with the compounds of the present invention include, but are not limited to, Estrogens: Diethylstibestrol Ethinyl estradiol (breast, prostate); Antiestrogen: Tamoxifen (breast); Androgens: Testosterone propionate Fluxomyesterone (breast); Antiandrogen: Flutamide (prostate); Gonadotropin-Releasing Hormone Analog: Leuprolide (prostate). Other hormones include medroxyprogesterone acetate, estradiol, megestrol acetate, octreotide acetate, diethylstilbestrol diphosphate, testolactone, and goserelin acetate. *Physicians' Desk Reference,* 50th Edition, 1996.

B. Anti-Psoriasis Agents

The compounds of the present invention can be used in combination or alternation with agents used to treat psoriasis including, but not limited to the following:

Topical treatments: corticosteroids (cortisone), calcipotriene (a synthetic form of vitamin $D_3$); coal tar; anthralin; topical retinoids (e.g. tazarotene, or Tazorac), UV light therapy.

Systemic drugs: Amevive (alefacept, LFA3TIP), Enbrel (etanercept), and Raptiva (efalizumab), Remicade (infliximab), Humira, ABX-IL8, Xanelim, psoralen, methotrexate, Tegison, Anti-CD4, Anti-IL2R (Simulect®, basiliximab), fusion proteins, HumaT4, HuMax-CD4, HuMax-IL15, IDEC-114, ISIS 2302, LFA-1 antagonists, methotrexate, MEDI-507 (siplizumab), p38 kindase inhibitors, Xerecept® (hCRF), Zenapax® (anti—CD25, daclizumab), cyclosporine (Neoral.RTM.), Hydroxyurea (Hydrea.RTM.), retinoids (e.g., acitretin (Soriatane.RTM.)) and antibiotics.

C. Anti-Inflammatory Bowel Disease (IBD) Agents

The compounds of the present invention can be used in combination or alternation with drugs or other agents used to treat IBD including, for example, aminosalicylates, corticosteroids, antibiotics and immunomodulators. Representative, non-limiting anti-IBD agents include:

Corticosteroids: Prednisone, Medrol®, methylprednisolone, hydrocortisone, budesonide (Entocort EC).

Aminosalicylates: sulfasalazine (Azulfidine), Rowasa, olsalazine (Dipentum®), mesalamine (Asacol,® Pentasa®), and balsalazide (Colazal,™), Balsalazide (Colazal™).

Immune System Modulators: azathioprine (Imuran), 6 mercaptopurine (Purinethol); cyclosporine A (Sandimmune®, Neoral®).

Biological therapy: Infliximab (Remicade)

Antibiotics: ciprofloxacin (Cipro, metronidazole (Flagyl), ampicillin, sulfonamide, cephalosporin, tetracycline, metronidazole, vancomycin, tobramycin.

Other agents including anti-TNF, interleukin-10 (IL-10), interferon beta, methotrexate, zinc, tacrolimus (FK506), mycophenolate mofetil, heparin, essential fatty acids (e.g., omega-3 fatty acids (Epanova™), 6-fatty acids), short chain fatty acids (SCFA) (e.g., butyrate), glutamine, phosphatidylcholine/phosphatidylinositol (PC/PI), superoxide dismutase (SOD), rosiglitazone, clotrimazole, Antegren(™) (natalizumab), CNI-1493, STA-5326, Adalimumab, G-CSF, melatonin, estrogen, dehydroepiandrosterone (DHEA), vitamin A, C, E, K, carotenoids, folic acid, calcium, iron, magnesium, selenium, metallothionein, copper, fiber, probiotics (e.g., Lactobacilli, Streptococci, Bifidobacteria, e coli), botanicals and flavinoids (e.g., ginkgo biloba, boswellia serrata, peumus boldus, plant sterols and sterolins, bromelain, quercetin, rutin).

D. Anti-Arthritis and Osteoarthritis Agents

The compounds of the present invention can be used in combination or alternation with therapeutic agents used to treat arthritis, including, for example, nonsteroidal anti-inflammatory drugs (NSAIDs), analgesics, biological response modifiers, corticosteroids or steroids, disease-modifying antirheumatic drugs (DMARDs), fibromyalgia medications, osteoporosis medications, and gout medications.

NSAIDs: carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some non-limiting examples of COX-2 inhibitors are Celebrex (celecoxib) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine, Hydrochloride, Bornyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucarnetacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

Analgesics: acetaminophen, opioid analgesics, transdermal fentanyl

Biological response modifiers: Etanercept (Enbrel), infliximab (Remicade), adalimumab (Humira), anakinra (Kineret)

Corticosteroids: glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex DMARDs: hydroxychloroquine (Plaquenil), cyclosphamide (Cytoxan), chlorambucil (Leukeran), the gold compound auranofin (Ridaura), sulfasalazine (Azulfidine) and minocycline (Dynacin, Minocin), cyclosporine (Sandimmune, Neoral), toll-like receptor agonists and antagonists. Other forms of DMARDs include immunosuppressants and tumor necrosis factor (TNF) blockers. Representative, non-limiting TNF blockers include etanercept (Enbrel), infliximab (Remicade) and adalimumab (Humira).

Another anti-rheumatic drug suitable for use in combination with the compound of the present invention is an Interleukin-1 receptor antagonist (IL-1Ra).

Fibromyalgia medications: amitriptyline (Elavil, Endep) and fluoxetine (Prozac); cylobenzaprine (Cycloflex, Flexeril), tramadol (Ultram), gabapentin (Neurontin), and dual-reputake inhibitors.

Osteoperosis medications: estrogens, parathyroid hormones (calcitonin) bisphosphonates (alendronate and risedronate sodium), selective receptor molecules (raloxifene hydrochloride) and bone formation agents (teriparatide).

Gout medications: allopurinol (Lopurin, Zyloprim), probenecid (Benemid, Probalan), losartan (Cozaar, Hyzaar), fenofibrate (Tricor).

Agents used to treat osteoarthritis, including but not limited to:

Analgesics (e.g., acetaminophen), Paracetamol, dextropropoxyphene, non-steroidal anti-inflammatory drug (NSAID) (e.g., Advil, Motrin IB, Aleve, ketoprofen, Ibuprofen and naproxen, aspirin), corticosteroids, Doxycycline, Kineret, MMP inhibitors, Hydroxychloroquine (Plaquenil) glucosamine, chondroitin, COX-2 inhibitors (e.g., Vioxx® (rofecoxib), Celebrex® (celecoxib), Bextra® (valdecoxib), hyaluronans, Hyalgan® (hyaluronan), Synvisc® (hylan G-F20), topical treatments (non-steroidal anti-inflammatory drugs, capsaicin).

E. Anti-Chronic Obstructive Pulmonary Disease Agents

The compounds of the present invention can be used in combination or alternation with therapeutic agents used to treat chronic obstructive pulmonary disease, including, but not limited to:

Bronchiodilator therapy: B2 adrenoreceptor agonists (e.g., salbutamol (Ventolin®, Ventodisk®) and terbutaline sulphate (Bricanyl), fenoterol hydrobromide (Berotec®), rimiterol hydrobromide (Pulmadil®), pirbuterol (Exirel®), reproterol hydrochloride (Bronchodil®) and tulobuterol hydrochloride (Brelomax®)), anticholinergic agents (Ipratropium bromide, Atrovent®, and Oxitropium bromide, Oxivent®, (Tiotropium bromide, Ba 679 BR).

Methylxanthines including theophylline (Theo-dur®, Phyllocontin®, Uniphyllin®).

Corticosteriods including beclomethasone dipropionate (Becotide®, Becloforte®) and budesonide (Pulmicort®), flunisolide inhalation, triamcinolone inhalation, fluticasone inhalation, beclomethasone inhalation, Prednisone, methylprednisolone.

Other agents include, for example, Combivent (ipratropium/salbutamol), Advair/Seretide (flucatisone/salmeterol), Symbicort (formoterol/budesonide), Asmanex (mometasone furoate), Foradil, Ariflo (cilomilast), ONO 6126, talnetant, 842470/AWD 12281, IC 485, CP 671305.

F. Anti-Asmtha Agents

The compounds of the present invention can be used in combination or alternation with therapeutic agents used to treat asmtha, including, for example:

Anti-allergics: cromolyn sodium (Intal, Lomudal, Nasalcrom, Novo-Cromolyn, Rynacrom, ketotifen fumarate (ketotifen fumarate).

Anti-inflammatories: including both non-steroidal and steroidal. Non-steroidal anti-inflammatories include, e.g., nedocromil (Tilade). Steroidal anti-inflammatories include, e.g., beclomethasone dipropionate (Aerobec, Beclovent, Beclodisk, Becloforte, Becodisk), budesonide (Pulmicort, Rhinocort), dexamethasone sodium phosophate (Decadron phosphate), flunisolide (Aerobid, Bronalide, Nasalide), fluticasone propionate, triamcinolone acetonide (Azmacort, Nasacort).

Anticholinergics: ipratropium bromide (Atrovent) belladonna alkaloids, Atrovent (ipratropium bromide), atropine, and oxitropium bromide.

Antihistimines: alkylamines, ethanolamines ethylenediamines, piperazines, piperidines or phenothiazines; Chlortrinmeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphen-hydramine), Tavist (clemastine), Dimetabs (dimenhydrinate, Dramamine, Mannine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

$\beta_2$-adrenergic agonists (beta agonists): albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

Leukotriene Receptor Antagonists: zafirlukast (Accolate); zileuton montelukast (Zyflo, Singulair).

Xanthines (bronchodilators): theophylline (e.g., Aerolate, Respbid, Slo-bid), dyphylline, oxtriphylline.

Combination medications: Advair (salmeterol, fluticasone), Aerocrom (cromolyn sodium, albuterol), Asbron G (theophylline sodium glycinate, guaifenesin (expectorant), Berodual (ipratropium HBr, fenoterol HBr), Bronkaid Caplets (ephedrine sulfate, guaifenesin), Combivent (salbutamol (albuterol), ipratropium bromide), Congess (guaifenesin, pseudoephedrine), Duo-Medihaler (isoproterenol hydrochloride, phenylephrine bitartrate), Duovent (fenoterol hydrobromide, ipratropium bromide), Marax (ephedrine sulfate, theophylline, Atarax (hydroxyzine HCl)), Primatene Tablets (theophylline, ephedrine HCl), Quadrinal (theophylline calcium salicylate, ephedrine HCl, phenobarbital, potassium iodide), Rynatuss (carbetapentane taniate, chlorpheniramine tannate, ephedrine tannate, phenylephrine tannate), Tedral (theophylline, ephedrine HCl, Phenobarbital), Ventolin-Plus (albuterol, beclomethasone, dipropionate).

Other anti-asthma agents suitable for use in combination or alternation with the antifolates of the present invention include xanthines and methylxanthines, such as Theo-24 (theophylline, Slo-Phylline, Uniphyllin, Slobid, Theo-Dur), Choledyl (oxitriphylline), aminophylline; phosphodiesterase inhibitors such as zardaverine; calcium antagonists such as nifedipine; and potassium activators such as cromakalim.

In one embodiment, the compound is administered in combination or alterantion with one or more prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

G. Anti-Multiple Sclerosis Agents

The antifolates of the present invention can be used in combination or alternation with agents used to treat multiple sclerosis, including for example: ReVia (Naltrexone), Pregabalin, Copaxone® (Glatiramer acetate), Provigil (Modafinil), Symmetrel (Amantadine), Rebif® (Interferon beta-1a), solu-Medrol (I.V. Methylprednisolone), Avonex® (Interferon beta-1a), Betaseron®(Interferon beta-1b). Other representative anti-multiple sclerosis agents for use in combination with the compounds of the present invention include:

Chemotherapetuic agents: Mitoxantrone (Novantrone), Azathioprine (Imuran), Cyclophosphamide (Cytoxan, Neosar), Cyclosporine (Sandimmune), methotrexate, Cladribine.

Corticosteroids and ACTH: MethylPrednisolone (Depo-Medrol), Prednisone (Deltasone), Prednisolone (Delta-Cortef), Dexamethasone (Medrol, Decadron), Adreno-corticotrophic Hormone (ACTH) and Corticotropin (Acthar).

Dysaesthesia agents: Carbamazepine (Tegretol, Epitol, Atretol, Carbatrol), Gabapentin (Neurotonin), Topiramate (Topamax), Zonisamide (Zonegran), Phenytoin (Dilantin), Amitriptyline (Elavil), Imipramine, Imipramine, Doxepin (Sinequan, Adapin, Triadapin, Zonalon), Protriptyline (Vivactil), Pentoxifylline (Trental), Ibprofen (Neurofen), aspirin, acetaminophen, Hydroxyzine.

Agents used to treat depression and insomnia: Fluoxetine (Prozac), Sertraline (Zoloft), Venlafaxine, Citalopram (Celexa), Parocetine (Paxil, Seroxat), Trazodone (Desyrel, Trialodine), Nortriptyline, Imipramine, Dothiepin, Lofepramine. Tranylcypromine, Moclobemide, Nefazodone, Mirtazapine, diazepam (Valium), alprazolam, Buspirone.

Agents used to treat fatigue: for example, amantadine (Symmetrel), pemoline (Cylert), and Modafinil.

Agents used to treat spasticity and muscle tics: Diazepam, Clonazepam, Baclofen, Dantrolene sodium, Dantrolene sodium, Clonidine, and Botulinum Toxin.

Agents used to treat tremors: Clonazepam, Gabapentin, Primidone, Botulinum toxin, Acetazolamide, Levodopashy, carbidopa, and Isoniazid.

Agents used to treat nausea and dizziness: Meclizine, Dimenhydrinate, Prochlorperazine, Scopolamine, and Diphenhydramine.

Antivirals and vaccinations: flu jabs and acyclovir.

Agents used to treat urinary problems: Oxybutynin, Desmopressin, Vasopressin, Tolterodine, carbamazepine, Imipramine, Bethane, Phenoxybenzamine, Terazosin, Propantheline, Oxybutynin, Hyoscyamine, Hyoscyamine, Diazepam, Methenamine, Nitrofurantoin, Phenazopyridine, Ciprofloxacin. Also agents used to treat bowel problems including, for example, Bisacodyl and Psyllium hydrophilic mucilloid Other agents and therapies include, for example, potassium channel blockers (e.g., 4-aminopyridine (4-AP and Fampridine), 3,4 Diaminopyridine, alpha-interferon, Alemtuzumab, anti-T-cell monoclonal antibodies, anti-lymphocyte globulin, IV Immunoglobin, Eliprodil, oral myelin (Myloral), cladribine (Leustatin, 2-CDA), cyclophosphamide (Cytoxan), Natalizumab, gamma-interferon, IL-2-toxin, mitoxantrone, gabapentin, and methylprednisolone, methotrexate, Pregabalin, Procarin (transdermal histamine), plasmapheresis (plasma exchange), PUVA (psoralen ultraviolet light), t-cell receptor therapy, t-cell vaccination, total lymphoid irradiation, transforming growth factor-beta (TGF), tumor necrosis factor antagonists, and Ziconotide.

The present invention is described by way of illustration, in the following examples. It will be understood that one of ordinary skill in that art that these examples are in no way limiting and that variation of detail can be made without departing from the spirit and scope of the invention.

EXAMPLES

Example 1

Inhibition of Dihydrofolate Reductase and Thymidylate Synthase

The ability of M-TREX to inhibit recombinant dihydrofolate reductase (DR) and thymidylate synthase (TS) in vitro studied in comparison to other antifolate drugs. The results are summarized in Table I:

| Compound | $I_{50}$ (human DHFR) | $I_{50}$ (Human TS) |
|---|---|---|
| MTX | $1.7 \times 10^{-8}$ M | — |
| TOMUDEX | — | $1.0 \times 10^{-6}$ M |
| MDAM | $4.4 \times 10^{-8}$ M | — |
| MTA (LY-231514) | $6.6 \times 10^{-6}$ M | $1.1 \times 10^{-5}$ M |
| M-TREX | $1.7 \times 10^{-8}$ M | $3.8 \times 10^{-6}$ M |

These results establish that M-TREX is a potent inhibitor of both DHFR and TS.

Example 2

Formulation of MTREX in a Microcrystalline Cellulose Capsule

Materials

Avicel PH 101 will be used to dilute the drug to the required dose strengths prior to capsule filling. Additional materials are listed in Table 1.

TABLE 1

| Material | Grade | Function | Supplier |
|---|---|---|---|
| Avicel PH101 (Microcrystalline Cellulose) | EP | Filler/Diluent | HONEYWILL & STEIN |
| White Hard Gelatin Capsules Size 0 | EP | Shell | CAPSUGEL |

A Semi-automated capsule filler, such as a Feton Plate and a blender, such as a Turbula-Drum will be used to formulate the drug.

Methods

LOD—Loss On Drying

The LOD will be measured using Sartorius MA45 infrared balance. The program selected for the analysis will be dependant on the physical properties of the drug. An appropriate sample size will be weighed out onto the aluminum tray of the LOD balance. Care will be taken to ensure that sample is leveled and in the middle of the tray, with no gaps. Using the appropriate method, the loss on drying analysis will be performed. The LOD value will be recorded in percentage.

Carr's Compressibility Index—Bulk/Tan Density

The sample will be added to a measuring cylinder to an appropriate volume. The weight and the volume of the sample will be recorded as $W_p$, poured weight and $V_p$, poured volume respectively. The cylinder will be place upon the jolting volumeter and oscillated for appropriate number of taps. The final volume of the sample will be recorded as $V_t$, tapped volume. The following calculations will be performed as per equations 1-3.

$$\text{Poured Density } (P_p) = (W_p/V_p) \quad \text{EQUATION 1}$$

$$\text{Tapped Density } (P_t) = (W_p/V_t) \quad \text{EQUATION 2}$$

$$\text{Carrs Compressibility Index (CCI)} = [(P_t - P_p)/P_t] \times 100 \quad \text{EQUATION 3}$$

Semi-Automated Capsule Filling Method

Probe formulations including placebo (Avicel PH1O1 only) detailed in Table 3, will be manufactured using a Turbula drum blender set to an appropriate mixing duration. Each formulation will undergo an encapsulation process feasibility study using semi-automated capsule filler—Feton plate. The content uniformity data, of the powder blend and the filled capsules will be determined.

Capsules will be prepared at the highest and lowest dosage strengths and these will be placed on accelerated stability. Additional powder blends characterization such as LOD and Carr's index, detailed will also be performed.

TABLE 3

| Materials | Function | mg/Capsule | mg/Capsule | mg/Capsule |
|---|---|---|---|---|
| MTREX | Drug | 1.0 | 2.5 | 5 |
| Avicel PH101 (Microcrystalline Cellulose) | Filler/Diluent | — | — | — |

Accelerated Stability Study

An accelerated stability study as outlined in Table 4, will be performed. Samples of the formulated drug will be placed at 25 C/60% RH and 40° C./75% RH for up to 8 weeks. Appearance, assay and degradation testing for active drug MTREX will be performed at initial, 4 and 8 week time-points. Note, all analysis will be performed by Quintiles Analytical Development group. Details of these methods will be covered by separate documents from this group.

TABLE 4

Outline of Stress Stability Program

| | Time-points/(weeks) | | |
|---|---|---|---|
| Conditions | 0 | 4 | 8 |
| 5° C. | T | S | S |
| 25° C./60% RH | n/a | T | T |
| 40° C./75% RH | n/a | T | T |

T—denotes test for Appearance, Assay and Degradation
S—Storage only will be tested if 25° C./60% RH fails.

All of the compositions, methods, and/or processes disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

We claim:

1. A pharmaceutical composition comprising a compound of the formula:

or its pharmaceutically acceptable salt, wherein:

if $Y^1$ and $Y^2$ are both oxygen, and $V^1$ and $V^2$ are both oxygen, then at least two of $R^1$, $R^2$, $R^3$, $R^4$, $R^5$, $R^6$ and $R^7$ are not H;

X is $CH_2$, $CHCH_3$, $CH(CH_2CH_3)$, NH, $NCH_3$, or $NR^7$;

$R^1$, $R^2$, $R^3$, $R^4$, and $R^7$ are independently selected from H, optionally substituted alkyl, optionally substituted alkenyl or alkynyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue, or an amino acid acyl residue;

$R^5$ and $R^6$ are independently selected from H, optionally substituted alkyl, optionally substituted alkenyl or alkynyl, lipid, phospholipid, carbohydrate, peptide, cholesterol, an amino acid residue, or other pharmaceutically acceptable leaving group that is capable of providing a —C(=Y)$V^-$ or —C(=Y)VH moiety when administered in vivo;

each $Y^1$, $Y^2$, and $Y^3$ independently is O, S, or $NJ^1$;

each $V^1$ and $V^2$ independently is O, S, or $NJ^1$;

each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$ and $J^2$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{101}$, $R^{102}$, and $R^{103}$ are independently hydrogen, alkyl, alkenyl, alkynyl, aryl, acyl, heteroaryl, heteroalkyl, hydroxyl, alkoxy, cyano, azido, halogen, nitro, $SO_2$, $SO_3$, thioalkyl, or amino; and a pharmaceutically acceptable carrier selected from microcrystalline cellulose or cyclodextrin.

2. The pharmaceutical composition of claim 1, further comprising a second therapeutic agent, the composition being provided as a single unit dose.

3. The pharmaceutical composition of claim 2, wherein the second therapeutic agent is an anti-neoplastic agent.

4. The pharmaceutical composition of claim 2, wherein the second therapeutic agent is selected from the group consisting of anti-angiogenic agents, alkylating agents, anti-metabolites, cytotoxic agents, and anti-rheumatoid arthritis agent.

5. The pharmaceutical composition of claim 2, wherein the second therapeutic agent is selected from the group consisting of non-steroidal anti-inflammatory agents, analgesics, corticosteroids and disease-modifying anti-rheumatic agents.

6. The pharmaceutical composition of claim 5, wherein the disease-modifying anti-rheumatic agent is a TNF blocker.

7. The pharmaceutical composition of claim 6, wherein the TNF blocker is selected from the group consisting of etanercept, infliximab, adalimumab, and CDP-870.

8. The pharmaceutical composition of claim 2, wherein the second therapeutic agent is an anti-autoimmune disease agent.

9. The pharmaceutical composition of claim 2, wherein the second therapeutic agent is selected from the group consisting of rituximab, abatacept, actemra, leflunomide, and methotrexate.

10. A pharmaceutical composition comprising a compound of the formula:

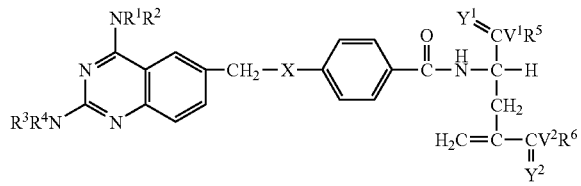

or its pharmaceutically acceptable salt, wherein:

if $Y^1$ and $Y^2$ are both oxygen, and $V^1$ and $V^2$ are both oxygen, then at least two of $R^1$, $R^2$, $R^3$, $R^4$, $R^5$, $R^6$ and $R^7$ are not H;

X is $CH_2$, $CHCH_3$, $CH(CH_2CH_3)$, NH, $NCH_3$, or $NR^7$;

$R^1$, $R^2$, $R^3$, $R^4$, and $R^7$ are independently selected from H, optionally substituted alkyl, optionally substituted alkenyl or alkynyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue, or an amino acid acyl residue;

$R^5$ and $R^6$ are independently selected from H, optionally substituted alkyl, optionally substituted alkenyl or alkynyl, lipid, phospholipid, carbohydrate, peptide, cholesterol, an amino acid residue, or other pharmaceutically acceptable leaving group that is capable of providing a —C(=Y)$V^-$ or —C(=Y)VH moiety when administered in vivo;

each $Y^1$, $Y^2$, and $Y^3$ independently is O, S, or $NJ^1$;

each $V^1$ and $V^2$ independently is O, S, or $NJ^1$;

each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$ and $J^2$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{101}$, $R^{102}$, and $R^{103}$ are independently hydrogen, alkyl, alkenyl, alkynyl, aryl, acyl, heteroaryl, heteroalkyl, hydroxyl, alkoxy, cyano, azido, halogen, nitro, $SO_2$, $SO_3$, thioalkyl, or amino;

a pharmaceutically acceptable carrier; and a second therapeutic agent;

the composition being provided as a single unit dose.

11. The pharmaceutical composition of claim 10, wherein the second therapeutic agent is an anti-autoimmune disease agent.

12. The pharmaceutical composition of claim 10, wherein the second therapeutic agent is selected from the group consisting of rituximab, abatacept, actemra, leflunomide, and methotrexate.

13. A compound of the formula:

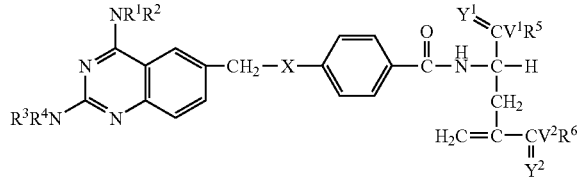

or its pharmaceutically acceptable salt, wherein:

if $Y^1$ and $Y^2$ are both oxygen, and $V^1$ and $V^2$ are both oxygen, then at least two of $R^1$, $R^2$, $R^3$, $R^4$, $R^5$, $R^6$ and $R^7$ are not H;

X is $CH_2$, $CHCH_3$, $CH(CH_2CH_3)$, NH, $NCH_3$, or $NR^7$;

$R^1$, $R^2$, $R^3$, $R^4$, and $R^7$ are independently selected from H, optionally substituted alkyl, optionally substituted alkenyl or alkynyl, acyl, —C(O)-(alkyl), —C(O)-(alkenyl), —C(O)-(alkynyl), —C(=$Y^3$)$V^3$, lipid, phospholipid, carbohydrate, peptide, cholesterol, an amino acid residue, or an amino acid acyl residue;

$R^5$ and $R^6$ are independently selected from H, optionally substituted $C_3$-$C_7$ alkyl, optionally substituted alkenyl or alkynyl, lipid, phospholipid, carbohydrate, peptide, cholesterol, an amino acid residue, or other pharmaceutically acceptable leaving group that is capable of providing a —C(=Y)V⁻ or —C(=Y)VH moiety when administered in vivo;

each $Y^1$, $Y^2$, and $Y^3$ independently is O, S, or $NJ^1$;

each $V^1$ and $V^2$ independently is O, S, or $NJ^1$;

each $V^3$ independently is OH, $OJ^1$, SH, $SJ^1$, $NH_2$, $NHJ^1$, $NJ^1J^2$, $CH_3$, $CH_2R^{101}$, $CHR^{101}R^{102}$, or $CR^{101}R^{102}R^{103}$;

each $J^1$ and $J^2$ independently are hydrogen, alkyl, alkenyl, alkynyl, alkaryl, cycloalkyl, aryl, cycloaryl, heteroalkyl, heterocycle, heteroaryl, hydroxyl, alkoxy, or amine; and each $R^{101}$, $R^{102}$, and $R^{103}$ are independently hydrogen, alkyl, alkenyl, alkynyl, aryl, acyl, heteroaryl, heteroalkyl, hydroxyl, alkoxy, cyano, azido, halogen, nitro, $SO_2$, $SO_3$, thioalkyl, or amino.

14. A pharmaceutical composition, comprising a compound according to claim 13 in combination with a pharmaceutically acceptable carrier.

15. The pharmaceutical composition of claim 14, further comprising a second therapeutic agent, the composition being provided as a single unit dose.

* * * * *

UNITED STATES PATENT AND TRADEMARK OFFICE
CERTIFICATE OF CORRECTION

| | | |
|---|---|---|
| PATENT NO. | : 7,829,708 B2 | Page 1 of 1 |
| APPLICATION NO. | : 11/223433 | |
| DATED | : November 9, 2010 | |
| INVENTOR(S) | : Michael J. Roberts and Simon Pedder | |

It is certified that error appears in the above-identified patent and that said Letters Patent is hereby corrected as shown below:

On the title page item (56) in the References cited, U.S. Patent Documents, a U.S. Patent Reference was omitted, please add U.S. Patent 4,818,753 4/1989 Colwell *et al.*

Column 19, Line 9, please change $-C(=Y)V^{31}$ to $-C(=Y)V^-$

Column 19, Line 45, please change $-C(=Y)V^{31}$ to $-C(=Y)V^-$

Column 20, Line 13, please change $-C(=Y)V^{31}$ to $-C(=Y)V^-$

Column 20, Line 23, please insert the word --each-- before $R^{100}, R^{101}, R^{102}$, and $R^{103}$ as follows:
 $\underline{each}$ $R^{100}, R^{101}, R^{102}$, and $R^{103}$ are independently hydrogen, alkyl, Column 20, Line 48, please change $-C(=Y)V^{31}$ to $-C(=Y)V^-$ Column 21, Line 54, please change $-C(=Y)V$ to $-C(=Y)V^-$ Column 23, Line 33, please change $-C(=Y)V^{31}$ to $-C(=Y)V^-$ Column 24, Line 13, please change $-C(=Y)V^{31}$ to $-C(=Y)V^-$ Column 24, Line 55, please change $-C(=Y)V^{31}$ to $-C(=Y)V^-$ Column 24, Line 60, please change $CR^{101}CR^{102} \ CR^{102}$ to $CR^{101}CR^{102} \ CR^{103}$ Column 25, Line 32, please change $-C(=Y)V^{31}$ to $-C(=Y)V^-$ Column 26, Line 10, please change $-C(=Y)V^{31}$ to $-C(=Y)V^-$ Column 26, Line 55, please change $-C(=Y)V^{31}$ to $-C(=Y)V^-$ Column 27, Line 29, please change $-C(=Y)V^{31}$ to $-C(=Y)V^-$ Column 28, Line 4, please change $-C(=Y)V^{31}$ to $-C(=Y)V^-$ Signed and Sealed this
Twenty-sixth Day of July, 2011

David J. Kappos
*Director of the United States Patent and Trademark Office*